US008088271B2

(12) United States Patent
Fujiwara et al.

(10) Patent No.: US 8,088,271 B2
(45) Date of Patent: Jan. 3, 2012

(54) METHOD OF MEASURING HEMATOCRIT (HCT), SENSOR USED IN THE METHOD, AND MEASURING DEVICE

(75) Inventors: Masaki Fujiwara, Matsuyama (JP); Teppei Shinno, Matsuyama (JP); Shin Ikeda, Katano (JP)

(73) Assignee: Panasonic Corporation, Osaka (JP)

( * ) Notice: Subject to any disclaimer, the term of this patent is extended or adjusted under 35 U.S.C. 154(b) by 1016 days.

(21) Appl. No.: 10/578,988

(22) PCT Filed: Dec. 3, 2004

(86) PCT No.: PCT/JP2004/018019
§ 371 (c)(1),
(2), (4) Date: May 11, 2006

(87) PCT Pub. No.: WO2005/054839
PCT Pub. Date: Jun. 16, 2005

(65) Prior Publication Data
US 2007/0062822 A1    Mar. 22, 2007

(30) Foreign Application Priority Data
Dec. 4, 2003    (JP) ................................ 2003-405481

(51) Int. Cl.
G01N 27/26    (2006.01)
G01N 33/487    (2006.01)
(52) U.S. Cl. ..................... 205/792; 205/777.5; 205/778; 204/403.01; 204/403.12
(58) Field of Classification Search .................. 204/409, 204/400–403.15; 205/777.5, 792, 775, 778
See application file for complete search history.

(56) References Cited

U.S. PATENT DOCUMENTS 3,922,598 A * 11/1975 Steuer et al. .................. 324/442
4,835,477 A    5/1989 Polaschegg et al.
4,897,162 A    1/1990 Lewandowski et al.
(Continued)

FOREIGN PATENT DOCUMENTS
EP    0 417 796    3/1991
(Continued)

OTHER PUBLICATIONS

Varlan, et al., "New design technique for planar conductometric haematocrit sensors", Sensors and Actuators B 34 (1996) 258-264.

*Primary Examiner* — Jeffrey T Barton
*Assistant Examiner* — Jennifer Dieterle
(74) *Attorney, Agent, or Firm* — Hamre, Schumann, Mueller & Larson, P.C.

(57) ABSTRACT

The present invention provides a method of electrochemically measuring a hematocrit (Hct) value using a sensor, capable of achieving excellent measurement accuracy and reliability and also provides a sensor used in the method. The method of electrochemically measuring a hematocrit (Hct) value of blood include: providing an electrode system having a working electrode (11) and a counter electrode (12), in which a redox substance is provided on the counter electrode (12) but not on the working electrode (11); supplying blood to the electrode system; applying a voltage to the electrode system in this state to cause an oxidation current or a reduction current to flow between the working electrode (11) and the counter electrode (12); detecting the oxidation current or the reduction current; and determining a Hct value based on a value of the detected current.

12 Claims, 32 Drawing Sheets

U.S. PATENT DOCUMENTS

| | | | |
|---|---|---|---|
| 5,264,103 A | | 11/1993 | Yoshioka et al. |
| 5,385,846 A * | | 1/1995 | Kuhn et al. ............... 205/777.5 |
| 5,463,435 A | | 10/1995 | Ezawa |
| 5,475,454 A | | 12/1995 | Ezawa |
| 5,582,697 A | | 12/1996 | Ikeda et al. |
| 6,287,451 B1 * | | 9/2001 | Winarta et al. ............ 205/777.5 |
| 6,340,428 B1 | | 1/2002 | Ikeda et al. |
| 6,541,216 B1 | | 4/2003 | Wilsey et al. |
| 6,599,407 B2 | | 7/2003 | Taniike et al. |
| 6,632,349 B1 * | | 10/2003 | Hodges et al. ............... 205/792 |
| 6,875,327 B1 | | 4/2005 | Miyazaki et al. |
| 7,018,843 B2 | | 3/2006 | Heller |
| 7,338,639 B2 | | 3/2008 | Burke et al. |
| 2001/0006149 A1 * | | 7/2001 | Taniike et al. ............... 204/403 |
| 2002/0048532 A1 | | 4/2002 | Lin et al. |
| 2002/0179442 A1 | | 12/2002 | Miyazaki et al. |
| 2003/0082076 A1 | | 5/2003 | Lin et al. |
| 2003/0098234 A1 * | | 5/2003 | Hasegawa et al. ....... 204/403.04 |
| 2003/0159945 A1 | | 8/2003 | Miyazaki et al. |
| 2004/0005721 A1 * | | 1/2004 | Tanike et al. ............... 436/518 |
| 2004/0043477 A1 | | 3/2004 | Schibli |
| 2004/0079652 A1 | | 4/2004 | Vreeke et al. |
| 2004/0134779 A1 | | 7/2004 | Hsu et al. |
| 2004/0173458 A1 | | 9/2004 | Noda et al. |
| 2004/0232009 A1 | | 11/2004 | Okuda et al. |
| 2005/0023137 A1 | | 2/2005 | Bhullar et al. |
| 2005/0145490 A1 | | 7/2005 | Shinno et al. |
| 2005/0164328 A1 | | 7/2005 | Kuwabata et al. |
| 2007/0080073 A1 | | 4/2007 | Wu et al. |
| 2007/0131565 A1 | | 6/2007 | Fujiwara et al. |
| 2007/0138026 A1 | | 6/2007 | Fujiwara et al. |
| 2010/0270177 A1 | | 10/2010 | Fujiwara |

FOREIGN PATENT DOCUMENTS

| | | |
|---|---|---|
| EP | 0 537 761 | 4/1993 |
| EP | 0 732 406 | 9/1996 |
| EP | 0 735 363 | 10/1996 |
| EP | 0 928 967 | 7/1999 |
| EP | 0 984 069 | 3/2000 |
| EP | 1 152 239 | 11/2001 |
| EP | 1 167 538 | 1/2002 |
| EP | 1 256 798 | 11/2002 |
| EP | 1 411 348 | 4/2004 |
| EP | 1 443 322 | 8/2004 |
| JP | 3-99254 | 4/1991 |
| JP | H11-194108 | 7/1997 |
| JP | 11-118794 | 4/1999 |
| JP | 2000-065778 | 3/2000 |
| JP | 2001-091512 | 4/2001 |
| JP | 2001-318071 | 11/2001 |
| JP | 2001-527215 | 12/2001 |
| JP | 3267933 | 1/2002 |
| JP | 3369183 | 11/2002 |
| JP | 2003-501627 | 1/2003 |
| JP | 2003-521708 | 7/2003 |
| JP | 2004-163411 | 6/2004 |
| JP | 2005-114359 | 4/2005 |
| JP | 2005-147990 | 6/2005 |
| WO | 94/29731 | 12/1994 |
| WO | 96/32883 | 10/1996 |
| WO | 97/16726 | 5/1997 |
| WO | 99/32881 | 7/1999 |
| WO | 00/73785 | 12/2000 |
| WO | 01/57510 | 8/2001 |
| WO | 03/008956 | 1/2003 |
| WO | 03/034055 | 4/2003 |
| WO | 03/076919 | 9/2003 |
| WO | 03/089658 | 10/2003 |
| WO | 2005/040407 | 5/2005 |

\* cited by examiner

METHOD OF MEASURING HEMATOCRIT (HCT), SENSOR USED IN THE METHOD, AND MEASURING DEVICE

TECHNICAL FIELD

The present invention relates to a method of measuring a Hct, a sensor used in the method, and a measuring device.

BACKGROUND ART

In clinical tests and the like, the Hct value of blood is measured as one index that helps to know properties of the blood (flowability, whether or not the subject has anemia, etc.). Furthermore, in blood component measurement such as measurement of a glucose concentration (a blood glucose level) in blood, a measured value may vary depending on a Hct value, so that the measurement of the Hct value might be required in order to correct the measured value. In general, the manual measurement of a Hct value is carried out, for example, by adding a blood coagulation inhibitor to blood, causing the blood to be drawn into a capillary tube, sealing one end of the tube with putty or the like, subjecting the tube to high speed centrifugation, and then determining the ratio of red blood cells to the blood as a whole as 100%, based on the height of the red blood cell column (such a method is called a "microhematocrit method"). Apart from the manual measurement, a Hct value also can be measured using an automatic blood cell counter. Examples of the method using an automatic blood cell counter include: those that recognize red blood cells as electrical pulses and calculate the Hct value from the sum of the sizes of the electrical pulses; and those that automatically calculate the Hct value from the average volume and the numbers of red blood cells. Incidentally, it is said that the standard Hct value of adult males is 39% to 50%, and the standard Hct value of adult females is 36% to 45%.

However, the conventional method for carrying out the manual Hct measurement has a problem in that it requires complicated operations and takes a long time. On the other hand, the Hct measurement method using an automatic blood cell counter has a problem in that it is necessary to use a special device. On this account, studies have been made to provide techniques for measuring a Hct value electrochemically and easily using a sensor (see Patent Document 1). However, the conventional method of measuring a Hct value using a sensor has a problem in its accuracy and reliability.
Patent Document 1: Japanese Patent No. 3369183

DISCLOSURE OF INVENTION

Problem to be Solved by the Invention

With the foregoing in mind, it is an object of the present invention to provide a method of electrochemically measuring a Hct value using a sensor, capable of achieving excellent measurement accuracy and reliability and also to provide a sensor used in the method and a measuring device.

Means for Solving Problem

In order to achieve the above object, the measurement method according to the present invention is a method of electrochemically measuring a hematocrit (Hct) value of blood, including: providing an electrode system having a working electrode and a counter electrode, in which a redox substance is provided on the counter electrode but not on the working electrode; supplying blood to the electrode system; applying a voltage to the electrode system in this state to cause an oxidation current or a reduction current to flow between the electrodes; detecting the oxidation current or the reduction current; and determining a Hct value of the blood based on the detected current value.

The sensor according to the present invention is a sensor for electrochemically measuring a hematocrit (Hct) value of blood, including an electrode system having a working electrode and a counter electrode, in which a redox substance is provided on the counter electrode but not on the working electrode. In this sensor, blood is supplied to the electrode system, a voltage is applied to the electrode system in this state to cause an oxidation current or a reduction current to flow between the electrodes, and a value of the oxidation current or the reduction current is detected.

The measuring device according to the present invention is a measuring device for measuring a Hct value, including: holding means for holding the sensor of the present invention; application means for applying a constant voltage to the electrode system of the sensor; and detection means for detecting the oxidation current or the reduction current flowing through the electrode system of the sensor.

Effects of the Invention

As described above, in the measurement method and the sensor of the present invention, the redox substance is provided on the counter electrode but not on the working electrode in the electrode system having the working electrode and the counter electrode. Thus, blood containing no redox substance is present on the working electrode. Therefore, according to the present invention, a reliable current value that depends on the Hct value of blood can be obtained by the working electrode, and this current value can be detected with high sensitivity by the redox substance on the counter electrode. As a result, the measurement can be carried out easily with excellent measurement accuracy. Moreover, the present invention can realize electrochemical measurement of a Hct value using a sensor, which eliminates the necessity of using a special large-scale measuring instrument or device as in the conventional measurement methods.

EXPLANATION OF REFERENCE NUMERALS

Figure 1:
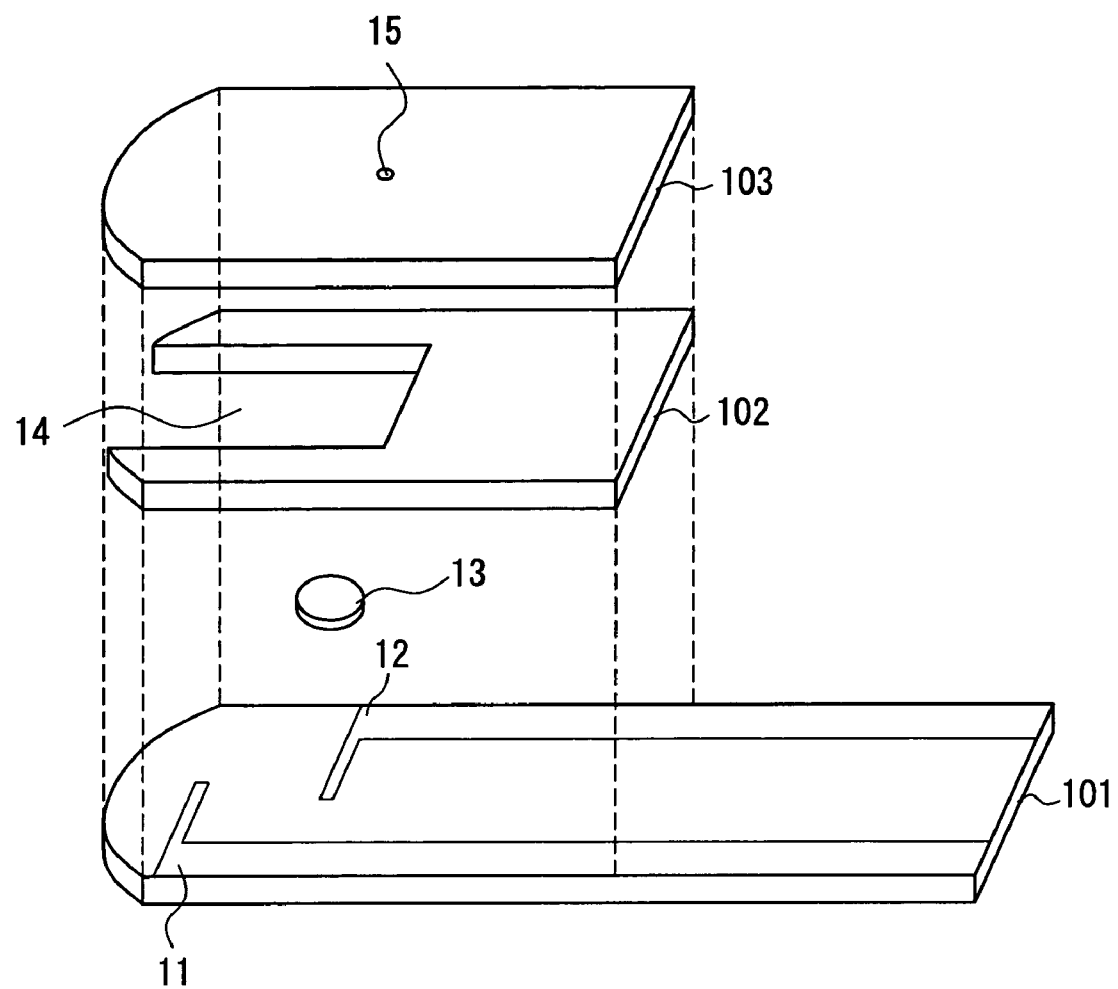
FIG. 1 is an exploded perspective view showing an example of a sensor according to the present invention.

| | |
|---|---|
| 11, 21, 31 | working electrode |
| 12, 22, 32 | counter electrode |
| 13, 23, 33 | reagent portion |
| 14, 24, 34 | channel |
| 15, 25, 35 | air vent hole |
| 101, 201 | insulating substrate |
| 102, 202 | spacer |
| 103, 203 | cover |
| 110, 123 | measuring device |
| 121 | sensor |
| 122 | sample supply port |
| 124 | display portion |
| 125 | attachment portion |
| 111a, 111b | connector |
| 112 | current/voltage conversion circuit |
| 113 | A/D conversion circuit |
| 114 | CPU |
| 115 | LCD |
| 116 | reference voltage source |

DESCRIPTION OF THE INVENTION

Hereinafter, the present invention will be described in detail.

In the method of measuring a Hct value and the sensor of the present invention, the redox substance is not particularly limited, and may be in a reduced state or an oxidized state. Examples of the redox substance include ferricyanides, p-benzoquinone, p-benzoquinone derivatives, phenazine methosulfate, methylene blue, ferrocene, and ferrocene derivatives. Among these, ferricyanides are preferable, and potassium ferricyanide is more preferable. Note here that a ferricyanide in the reduced state is a ferrocyanide, and potassium ferricyanide in the reduced state is potassium ferrocyanide. The amount of the redox substance to be blended is not particularly limited, but is, for example, 0.1 to 1000 mM, preferably 1 to 500 mM, and more preferably 10 to 200 mM per one measurement or one sensor. Moreover, it should be noted here that, when a material that can be oxidized or reduced relatively easily through electrolysis, such as silver, copper, or silver chloride, is used as an electrode material, an effect to be achieved by the present invention also can be obtained.

In the method of measuring a Hct value and the sensor of the present invention, the working electrode on which the redox substance is not provided preferably is coated with a polymeric material in order to prevent adhesion of impurities, oxidation of the working electrode, and the like. Examples of the polymeric material include carboxymethyl cellulose (CMC), hydroxyethyl cellulose, hydroxypropyl cellulose, methyl cellulose, ethyl cellulose, ethyl hydroxyethyl cellulose, carboxyethyl cellulose, polyvinyl alcohol, polyvinylpyrrolidone, polyamino acid such as polylysine, polystyrene sulfonate, gelatin and derivatives thereof, polyacrylic acid and salts thereof, polymethacrylic acid and salts thereof, starch and derivatives thereof, maleic anhydride polymer and salts thereof, and agarose gel and derivatives thereof. They may be used individually or two or more of them may be used together. The method of coating the electrode with a polymeric material is not particularly limited. For example, the coating can be achieved by providing a polymeric material solution, applying the solution to the electrode surface, and then removing a solvent contained in the coating layer of the solution by drying.

In the method of measuring a Hct value and the sensor of the present invention, a voltage applied between the electrodes preferably is equal to or higher than a voltage causing electrolysis of water, more preferably in the range from 1 to 10 V, and still more preferably in the range from 1 to 6.5 V. By applying a voltage that is equal to or higher than a voltage causing electrolysis of water, a current depending on a hematocrit can be measured with a still higher sensitivity. As a result, it is possible to obtain a stable current that is not affected by other redox substances present in blood and thus does not vary depending on a specimen (an individual). Furthermore, a voltage that is negative with respect to a voltage applied to the counter electrode may be applied to the working electrode. The voltage is applied for, for example, 0.001 to 60 seconds, preferably 0.01 to 10 seconds, and more preferably 0.01 to 5 seconds.

In the method of measuring a Hct value and the sensor according to the present invention, it is preferable that the shortest distance between the working electrode and the counter electrode is at least 0.05 mm. When the distance between the electrodes is at least 0.05 mm as described above, the reliability of the measured value is improved. More preferably, the distance between the electrodes is at least 0.1 mm, still more preferably at least 0.5 mm.

The sensor for measuring a Hct value according to the present invention preferably is configured so that it further includes an insulating substrate, the electrode system and a channel for leading blood thereto are formed on the insulating substrate, and one end of the channel communicates with the electrode system and the other end of the channel is open toward the outside of the sensor so as to serve as a blood supply port. In this case, the sensor may be configured so that it further includes a spacer and a cover and the cover is disposed on the insulating substrate via the spacer.

In the sensor for measuring a Hct value according to the present invention, a crystal homogenizing agent may further be provided on the electrode system.

The crystal homogenizing agent serves to homogenize the crystal condition of a reagent portion. As the crystal homogenizing agent, an amino acid may be used, for example. Examples of the amino acid include glycine, alanine, valine, leucine, isoleucine, serine, threonine, methionine, asparagine, glutamine, arginine, lysine, histidine, phenylalanine, tryptophan, proline, sarcosine, betaine, taurine, and salts, substitution products, and derivatives of these amino acids. They may be used individually or two or more of them may be used together. Among these, glycine, serine, proline, threonine, lysine, and taurine are preferable, and taurine is more preferable. The amount of the crystal homogenizing agent to be blended is, for example, 0.1 to 1000 mM, preferably 10 to 500 mM, and more preferably 10 to 300 mM per one measurement or one sensor.

Next, in the measuring device of the present invention, it is preferable that a voltage applied by the application means is equal to or higher than a voltage causing electrolysis of water, and the measuring device further includes calculation means for calculating a Hct value based on a value of the current detected by the detection means. Furthermore, for the same reason as that described above, the applied voltage preferably is in the range from 1 to 10 V, more preferably from 1 to 6.5 V.

In the following, an example of a sensor for measuring a Hct according to the present invention will be described with reference to the drawings.

Figure 2:
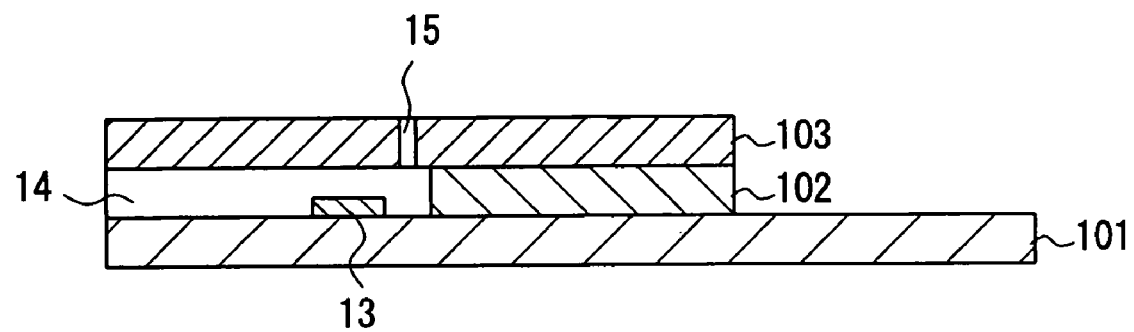
FIG. 2 is a sectional view of the sensor.
Figure 3:
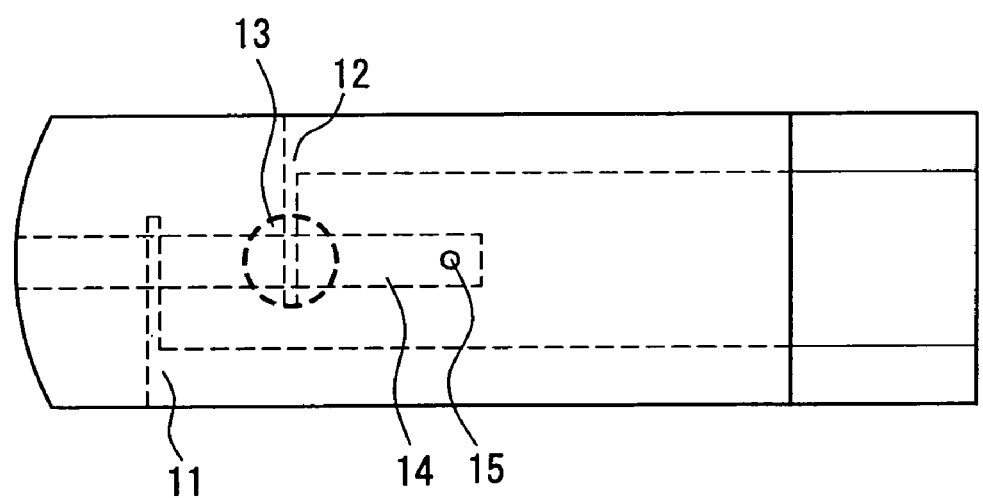
FIG. 3 is a plan view of the sensor.

FIGS. 1, 2, and 3 show an example of a sensor for measuring a Hct value according to the present invention. FIG. 1 is an exploded perspective view of the sensor, FIG. 2 is a sectional view of the sensor, and FIG. 3 is a plan view of the sensor. In these three drawings, the same components are given the same reference numerals.

As shown in the drawings, in this sensor, a working electrode 11 and a counter electrode 12 are formed in series on an insulating substrate 101. As described above, the surface of the working electrode 11 preferably is coated with a polymeric material. Furthermore, in the sensor of this example, a redox substance 13 is provided on the counter electrode 12. A cover 103 is disposed on the insulating substrate 101 so as to cover an entire area excluding one end portion (the end portion on the right in the drawings) with a spacer 102 intervening therebetween. This sensor has a channel 14 for leading blood to the working electrode 11 and the counter electrode 12. The channel extends to the other end portion (the end portion on the left in the drawings) of the sensor, and the tip of the channel is open toward the outside of the sensor so as to serve as a blood supply port. The working electrode 11 and the counter electrode 12 are connected to leads, respectively. These leads extend to the above-described one end portion (the end portion on the right in the drawings) of the sensor with the tip of each lead not being covered with the cover but being exposed. The cover 103 has an air vent hole 15 for causing capillary action at a portion corresponding to the end portion of the channel 14.

In the present invention, the material of the insulating substrate is not particularly limited, and may be, for example, polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), polymethyl methacrylate (PEA), an ABS resin (ABS), or glass. Among these, polyethylene terephthalate (PET), polycarbonate (PC), and polyimide (PI) are preferable, and polyethylene terephthalate (PET) is more preferable. The size of the insulating substrate is not particularly limited. For example, in the case where the insulating substrate has a plate-like shape as shown in the drawings, the insulating substrate may have an overall length of 5 to 100 mm, a width of 3 to 50 mm, and a thickness of 0.05 to 2 mm; preferably an overall length of 10 to 50 mm, a width of 3 to 20 mm, and a thickness of 0.1 to 1 mm; and more preferably an overall length of 10 to 30 mm, a width of 3 to 10 mm, and a thickness of 0.1 to 0.6 mm.

The electrodes and the leads on the insulating substrate may be formed by, for example, forming a conductive layer with gold, platinum, palladium, or the like by sputtering or vapor deposition and then processing the conductive layer into a particular electrode pattern with a laser. Examples of the laser include YAG lasers, $CO_2$ lasers, and excimer lasers.

The coating of the electrode surface with the polymeric material can be achieved by, for example, dissolving a predetermined polymeric material in water or a buffer solution and then drying it, as described above. For example, this can be achieved by dropping 0.01 to 100 mg of a 0.01 to 2.0 wt % CMC aqueous solution on the working electrode 11 on the substrate and then drying it. The method of drying is not particularly limited, and may be natural drying or forced drying using warm air.

The redox substance 13 can be provided on the counter electrode 12 by, for example, dissolving the redox substance in water or a buffer solution, dropping or applying the thus-obtained solution with respect to the electrode surface, and then drying it. In the case where other reagents are to be provided in addition to the redox substance, this can be achieved by preparing a reagent solution containing these reagent, dropping or applying the solution with respect to the electrode surface of the counter electrode, and then drying it, as described above. For example, this can be achieved by preparing a reagent solution by dissolving, in a 0.01 to 2.0 wt % CMC aqueous solution, potassium ferricyanide so that its concentration becomes 10 to 200 mM and taurine so that its concentration becomes 10 to 300 mM, dropping 0.01 to 100 mg of the thus-obtained reagent solution on the counter electrode 12 of the substrate, and then drying it. The drying method is not particularly limited, and may be natural drying or forced drying using warm air.

In the present invention, the material of the spacer is not particularly limited. For example, the same material as that of the insulating substrate can be used. The size of the spacer also is not particularly limited. For example, when the spacer has a shape as shown in the drawings, the spacer may have an overall length of 5 to 100 mm, a width of 3 to 50 mm, and a thickness of 0.01 to 1 mm; preferably an overall length of 10 to 50 mm, a width of 3 to 20 mm, and a thickness 0.05 to 0.5 mm; and more preferably an overall length of 10 to 30 mm, a width of 3 to 10 mm, and a thickness of 0.05 to 0.25 mm. The spacer has a cut-away portion that serves as the channel for leading blood. The size of the cut-away portion is as follows, for example: the length from the blood supply port to its end is 0.5 to 50 mm and the width is 0.1 to 10 mm; preferably the length from the blood supply port to its end is 1 to 10 mm and the width is 0.5 to 5 mm; and more preferably the length from the blood supply port to its end is 1 to 5 mm and the width is 0.5 to 2 mm. The cut-away portion may be formed, for instance, by using a laser, a drill, or the like, or by forming the spacer using a die that can form the spacer provided with the cut-away portion.

In the present invention, the material of the cover is not particularly limited. For example, the same material as that of the insulating substrate can be used. It is more preferable that a portion of the cover corresponding to the ceiling of the sample supply channel is subjected to a treatment for imparting hydrophilicity. The treatment for imparting hydrophilicity may be carried out by, for example, applying a surfactant or introducing a hydrophilic functional group such as a hydroxyl group, a carbonyl group, or a carboxyl group to the surface of the cover by plasma processing or the like. The size of the cover is not particularly limited. For example, when the cover has a shape as shown in the drawings, the cover may have an overall length of 5 to 100 mm, a width of 3 to 50 mm, and a thickness of 0.01 to 0.5 mm; preferably an overall length of 10 to 50 mm, a width of 3 to 20 mm, and a thickness of 0.05 to 0.25 mm; and more preferably an overall length of 15 to 30 mm, a width of 5 to 10 mm, and a thickness of 0.05 to 0.2 mm. The cover preferably has an air vent hole. The shape of the air vent hole may be, for example, circular, oval, polygonal, or the like, and the maximum diameter thereof may be, for example, 0.01 to 10 mm, preferably 0.025 to 5 mm, and more preferably 0.025 to 2 mm. The cover may have a plurality of air vent holes. The air vent hole may be formed, for instance, by perforating the cover with a laser, a drill, or the like, or by forming the cover using a die that can form the cover provided with the air vent hole.

Then, by laminating the insulating substrate, the spacer, and the cover in this order and integrating them, the sensor can be obtained. The integration can be achieved by adhering these three components with an adhesive or through heat-sealing. As the adhesive, an epoxy adhesive, an acrylic adhesive, a polyurethane adhesive, a thermosetting adhesive (a hot melt adhesive or the like), a UV curable adhesive, or the like can be used, for example.

Measurement of a Hct value using this sensor can be carried out in the following manner, for example. First, a fingertip or the like is punctured with a dedicated lancet to cause bleeding. On the other hand, the sensor is set in a dedicated measuring device (a meter). The blood supply port of the sensor set in the measuring device is brought into contact with the blood that has come out, so that the blood is led inside the sensor by capillary action. Then, by applying a constant voltage between the working electrode 11 and the counter electrode 12, oxidation of blood components occurs in the working electrode 11 while the reduction of the reduced substance that is in the oxidized state occurs in the counter electrode 12. Since the current flowing at this time depends on the Hct value, the Hct is determined by detecting this current. The Hct value can be determined from the detected current by providing a calibration curve or a calibration curve table for showing a relationship between a current and a Hct value beforehand and converting the detected current to the Hct value using the calibration curve or the calibration curve table each time the current is detected. As described above, the applied voltage is, for example, equal to or higher than a voltage causing electrolysis of water, preferably 1 to 10 V, and more preferably 1 to 6.5 V, and the voltage is applied for, for example, 0.001 to 60 seconds, preferably 0.01 to 10 seconds, and more preferably 0.01 to 5 seconds. In this step, since the working electrode 11 and the counter electrode 12 are spaced apart from each other by a certain distance and the redox substance is not present on the working electrode 11, a current that depends only on the Hct value of the blood flows and the redox substance present on the counter electrode 12 can suppress the reaction occurring at the counter electrode 12 from being a rate-determining step.

Figure 4:
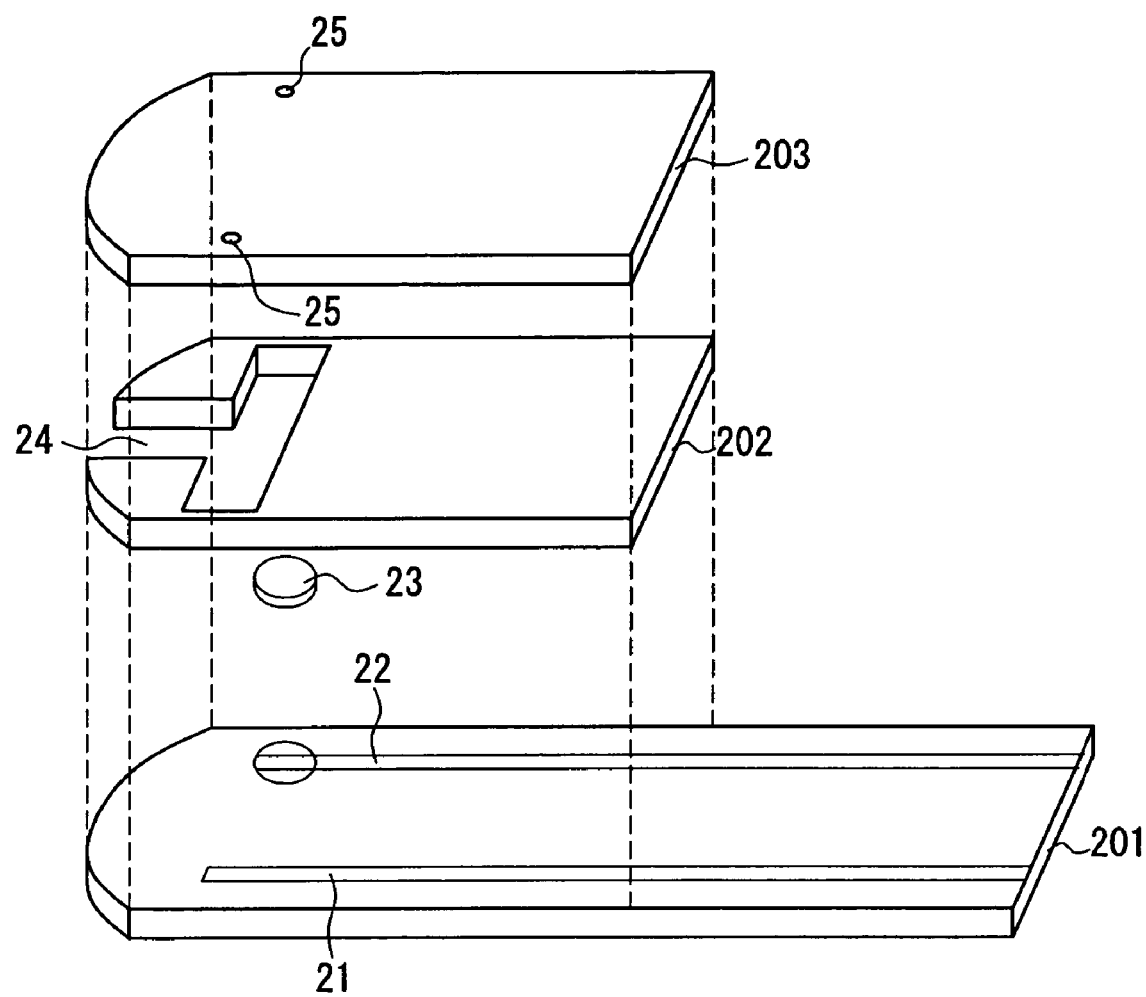
FIG. 4 is an exploded perspective view showing another example of a sensor according to the present invention.
Figure 5:
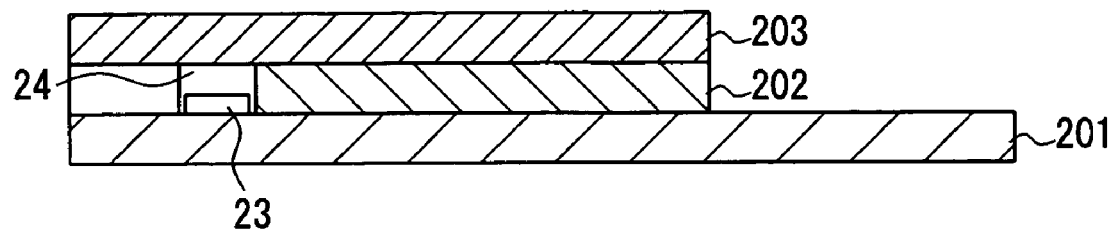
FIG. 5 is a sectional view of the sensor.
Figure 6:
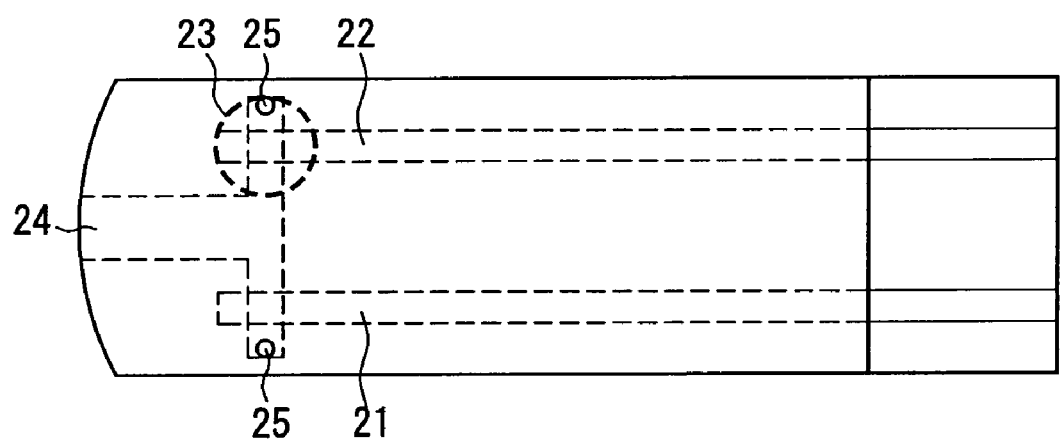
FIG. 6 is a plan view of the sensor.

Next, FIGS. 4, 5, and 6 show another example of a sensor for measuring a Hct value according to the present invention. FIG. 4 is an exploded perspective view of the sensor, FIG. 5 is a sectional view of the sensor, and FIG. 6 is a plan view of the sensor. In these three drawings, the same components are given the same reference numerals.

As shown in the drawings, in this sensor, a working electrode 21 and a counter electrode 22 are formed in parallel on a substrate 201, and a redox substance 23 is provided on the counter electrode 22. Thus, a channel 24 for leading blood to the electrodes extends from a blood inlet port at the tip of the sensor toward the center of the sensor and then branches into two portions so that the channel as a whole forms a shape. The working electrode 21 and the counter electrode 22 are located at the end portions of the branched portions, respectively. A spacer 202 has a cut-away portion that is also in a T-shape, and air vent holes 25 for causing capillary action are formed at portions of a cover 203 corresponding to end portions of the two branched portions of the channels. Except for the above, this sensor has the same configuration as the sensor of the above example, and the materials, production method, method of measuring a Hct value, measurement conditions, etc. for this sensor are the same as those for the sensor of the above example.

Although two examples of the sensor according to the present invention are given in the above, the electrode pattern in the sensor of the present invention is not limited to those shown in these examples. Furthermore, the sensor of the present invention may be incorporated in a sensor for measuring a blood component.

Figure 33:
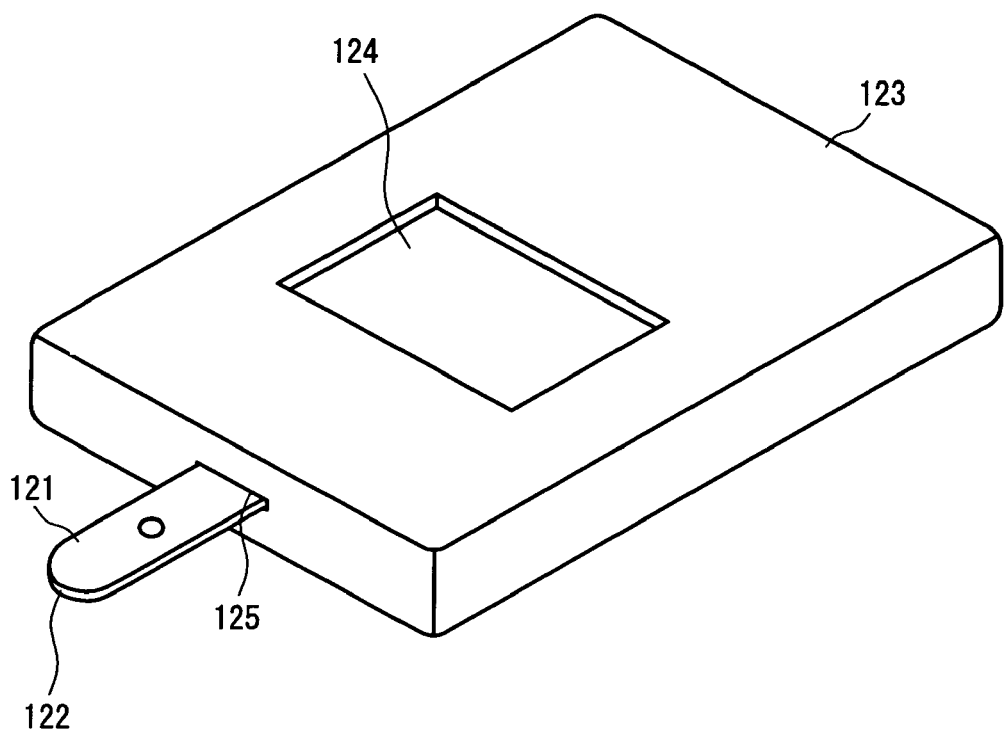
FIG. 33 is a perspective view showing an example of a measuring device according to the present invention.
Figure 34:
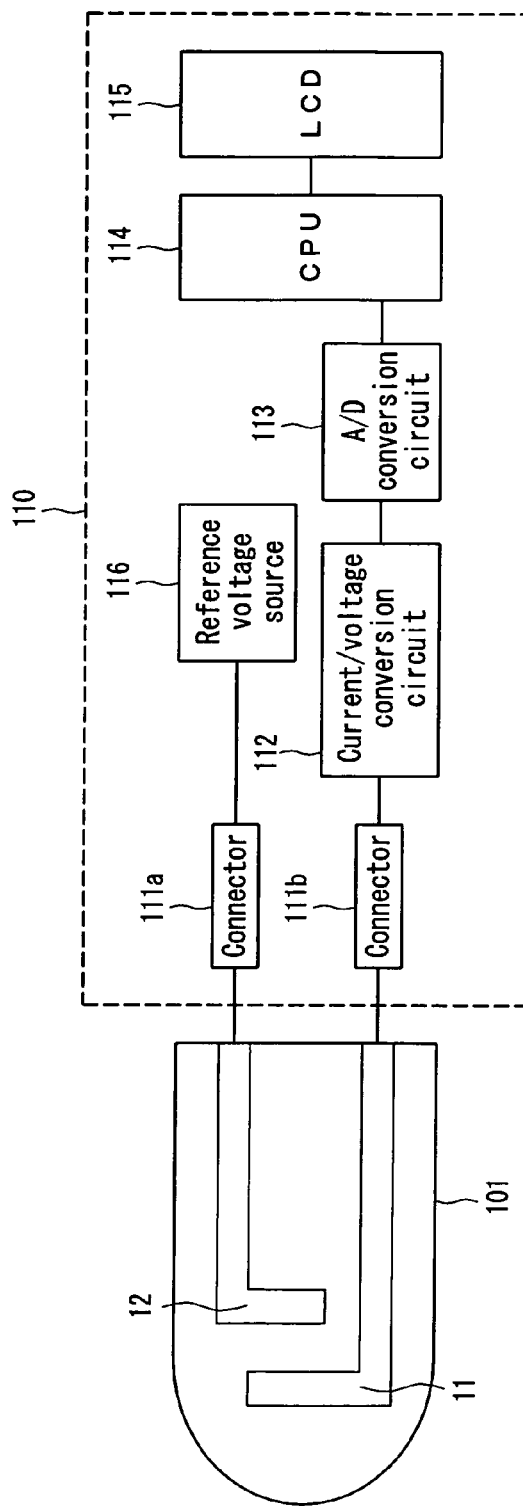
FIG. 34 shows the schematic configuration of the measuring device according to the above example.

In the following, an example of the measuring device according to the present invention will be described with reference to FIGS. 33 and 34. In FIGS. 33 and 34, the same components as those shown in FIGS. 1 to 6 are given the same reference numerals.

FIG. 33 is a perspective view showing an example of a measuring device according to the present invention to which a sensor is attached. As shown in FIG. 33, this measuring device 123 has a sensor attachment portion 125 at one end, and a sensor 121 is attached to this portion so as to be held by the measuring device. The reference numeral 122 denotes a sample supply port of the sensor 121. This measuring device 123 has a display portion 124 at a substantially center portion thereof, and the result of the measurement is displayed in this display portion 124.

Next, FIG. 34 shows an example of the configuration of a measuring device of the present invention. As shown in FIG. 34, this measuring device 110 includes, as main components, two connectors 111a and 111b, a current/voltage conversion circuit 112, an A/D conversion circuit 113, a CPU 114, a liquid crystal display (LCD) 115, and a reference voltage source 116. Note here that the reference voltage source 116 can be grounded. A counter electrode 12 of a sensor is connected to the reference voltage source 116 via the connector 111a. A working electrode 11 of the sensor is connected to the CPU 114 via the connector 111b, the current/voltage conversion circuit 112, and the A/D conversion circuit 113. The liquid crystal display 115 also is connected to the CPU. In this measuring device, the measurement of a hematocrit is carried out in the following manner, for example. First, when blood is supplied to an electrode system of the sensor, a constant voltage is applied between the working electrode 11 and the counter electrode 12 from the current/voltage conversion circuit 112 and the reference voltage source 116 for a certain period of time in accordance with an instruction from the CPU 114. The preferable range of the voltage applied between the electrodes is as described above. The application of the voltage causes an oxidation current or a reduction current to flow between the electrodes. This current is based on the hematocrit value of the blood. Thereafter, this current is converted into a voltage by the current/voltage conversion circuit 112, and the value of this voltage is converted into a digital value by the A/D conversion circuit 113 and is output to the CPU 114. The CPU 114 calculates a response value based on the digital value, converts the response value into a hematocrit value, and displays the result in the liquid crystal display 115.

Hereinafter, examples of the present invention will be described along with comparative examples.

Example 1

Figure 7:
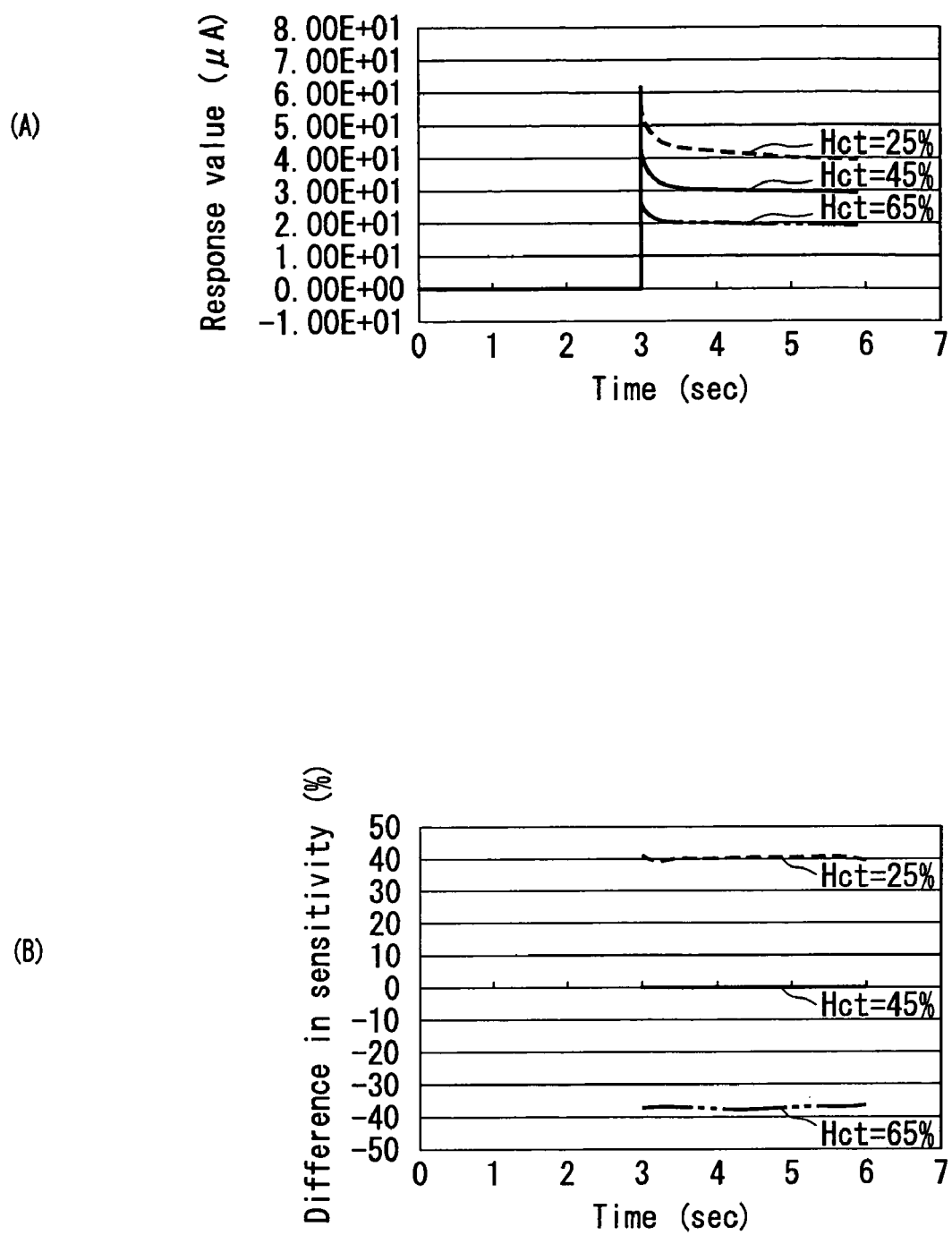
FIG. 7A is a graph showing changes in response current (μA) over time during voltage application in still another example of a sensor according to the present invention.
FIG. 7B is a graph showing changes in difference in sensitivity (%) over time during the voltage application in the example.

A sensor having a configuration as shown in FIGS. 1, 2, and 3 was produced. In this sensor, a working electrode 11 was coated with CMC. On the other hand, a reagent solution prepared by dissolving potassium ferricyanide (amount: 60 mM) and taurine (80 mM) in a CMC aqueous solution (0.1 wt %) was dropped on a counter electrode 12 and then dried. The shortest distance between the electrodes was set to be at least 1.0 mm. On the other hand, three types of blood samples whose Hct values were adjusted so as to be 25, 45, and 65, respectively, were provided. With regard to each of these three blood samples, a current flowing between the electrodes of the sensor when a voltage of 2.5 V was applied for 3 seconds was measured using the sensor. The results are shown in the graphs of FIGS. 7A and 7B. FIG. 7A is a graph showing changes in response current (μA) over time during the application of the voltage (V), and FIG. 7B is a graph showing changes in difference in sensitivity (%) over time during the application of the voltage (V). Note here that the graph showing the difference in sensitivity shows changes in blood response value over time with regard to the blood samples having Hct values of 25% and 65% relative to the same with regard to the blood sample having a Hct value of 45%. As shown in FIGS. 7A and 7B, according to this sensor, the difference in sensitivity did not depend on the voltage application time, and the response current reflecting the Hct value could be detected definitely. Moreover, even in the case where a polymeric material such as CMC was not present on the electrodes, it was still possible to detect the current.

Comparative Example 1

Figure 8:
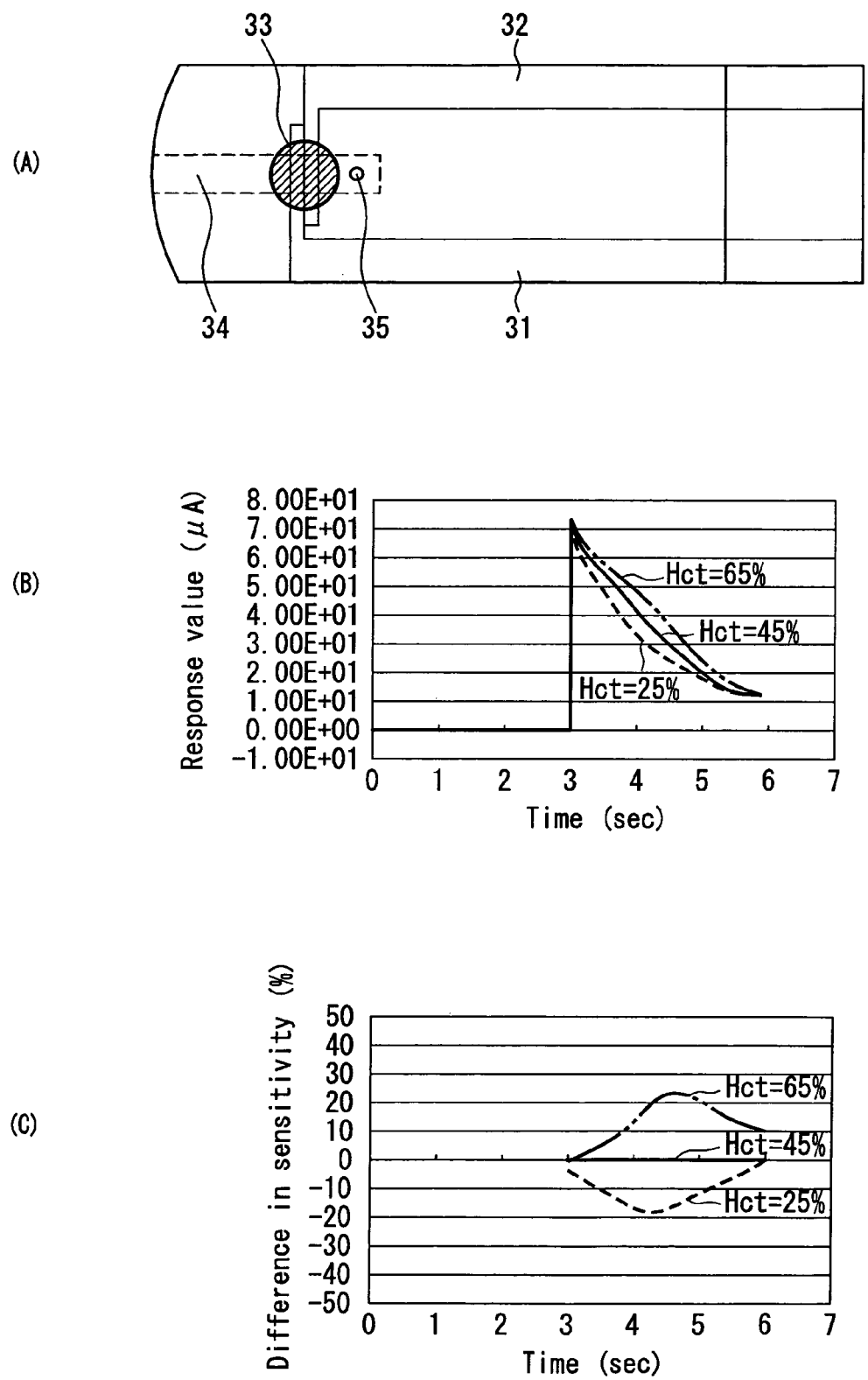
FIG. 8A shows how a redox substance is provided in a sensor according to a comparative example.
FIG. 8B is a graph showing changes in response current (μA) over time during voltage application in the comparative example.
FIG. 8C is a graph showing changes in difference in sensitivity (%) over time during the voltage application in the comparative example.

A sensor having a configuration as shown in FIG. 8A was produced. As shown in FIG. 8A, in this sensor, a working electrode 31 and a counter electrode 32 are formed so as to be in contact with each other on a channel 34, and an air vent hole 35 for causing capillary action is formed at a portion of a cover (not shown) corresponding to the end portion of the channel 34. In this sensor, a reagent solution was prepared by dissolving, in a 0.01 to 2.0 wt % CMC aqueous solution, potassium ferricyanide so that its concentration became 10 to 200 mM, potassium ferrocyanide so that its concentration became about ½ of that of the potassium ferricyanide, and taurine so that its concentration became 10 to 300 mM. This reagent solution was dropped on the working electrode 31 and the counter electrode 32 on a substrate so that the droplet of the reagent solution extended to the outside of the electrodes and then dried. Furthermore, the applied voltage was 0.2 V. Except for the above, the current flowing between the electrodes of the sensor was measured under the same measurement conditions as in Example 1 with regard to the above-noted three samples having the different Hct values. The results are shown in the graphs of FIGS. 8B and 8C. FIG. 8B is a graph showing changes in response current (μA) over time during the application of the voltage (V); and FIG. 8C is a graph showing changes in difference in sensitivity (%) over time during the application of the voltage (V). As shown in FIGS. 8B and 8C, in this comparative example, the difference in sensitivity was affected greatly by the voltage application time, so that the response current suitable for quantifying a Hct could not be obtained.

Comparative Example 2

Figure 9:
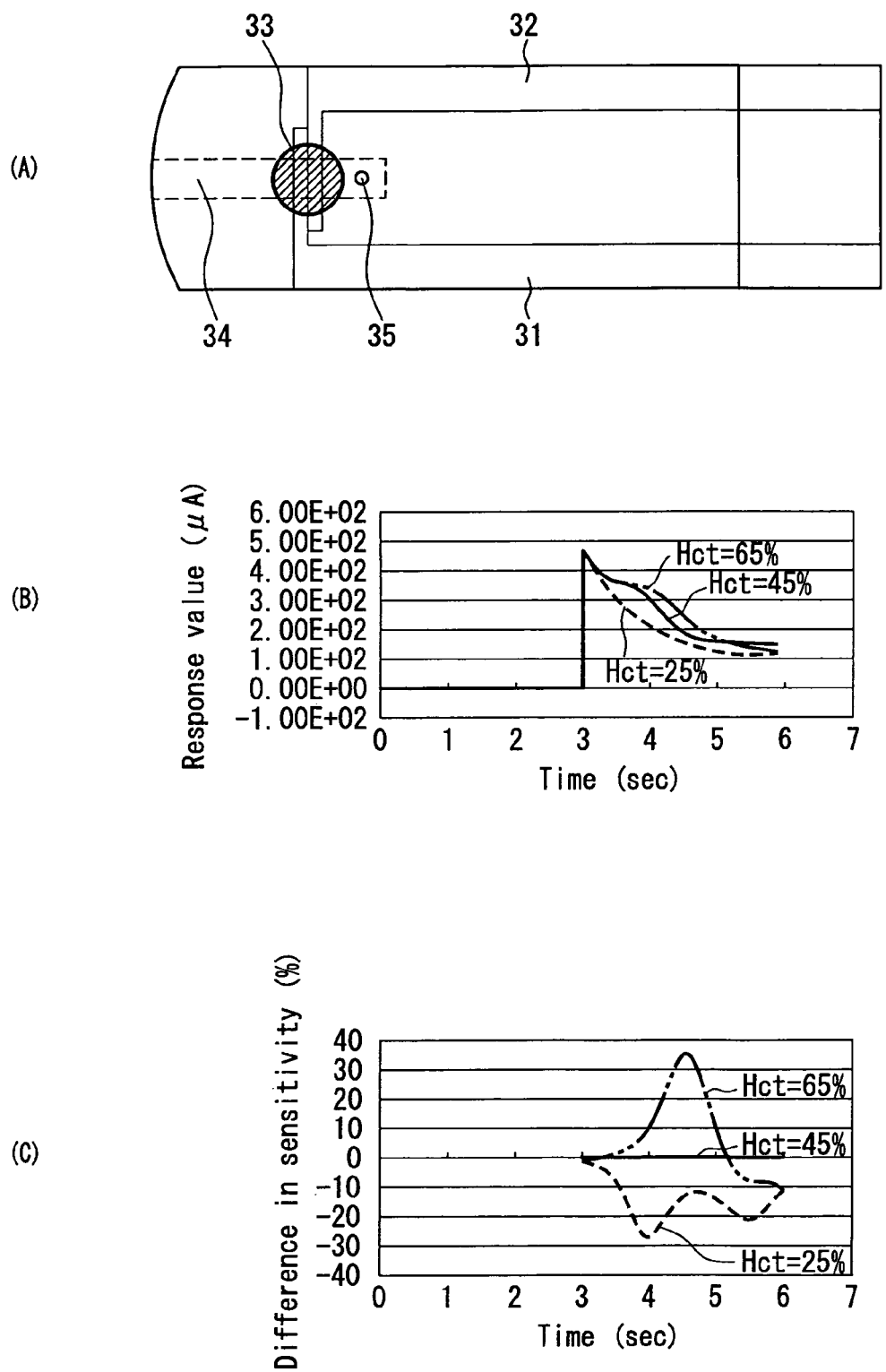
FIG. 9A shows how a redox substance is provided in a sensor according to another comparative example.
FIG. 9B is a graph showing changes in response current (μA) over time during voltage application in the comparative example.
FIG. 9C is a graph showing changes in difference in sensitivity (%) over time during the voltage application in the comparative example.
Figure 10:
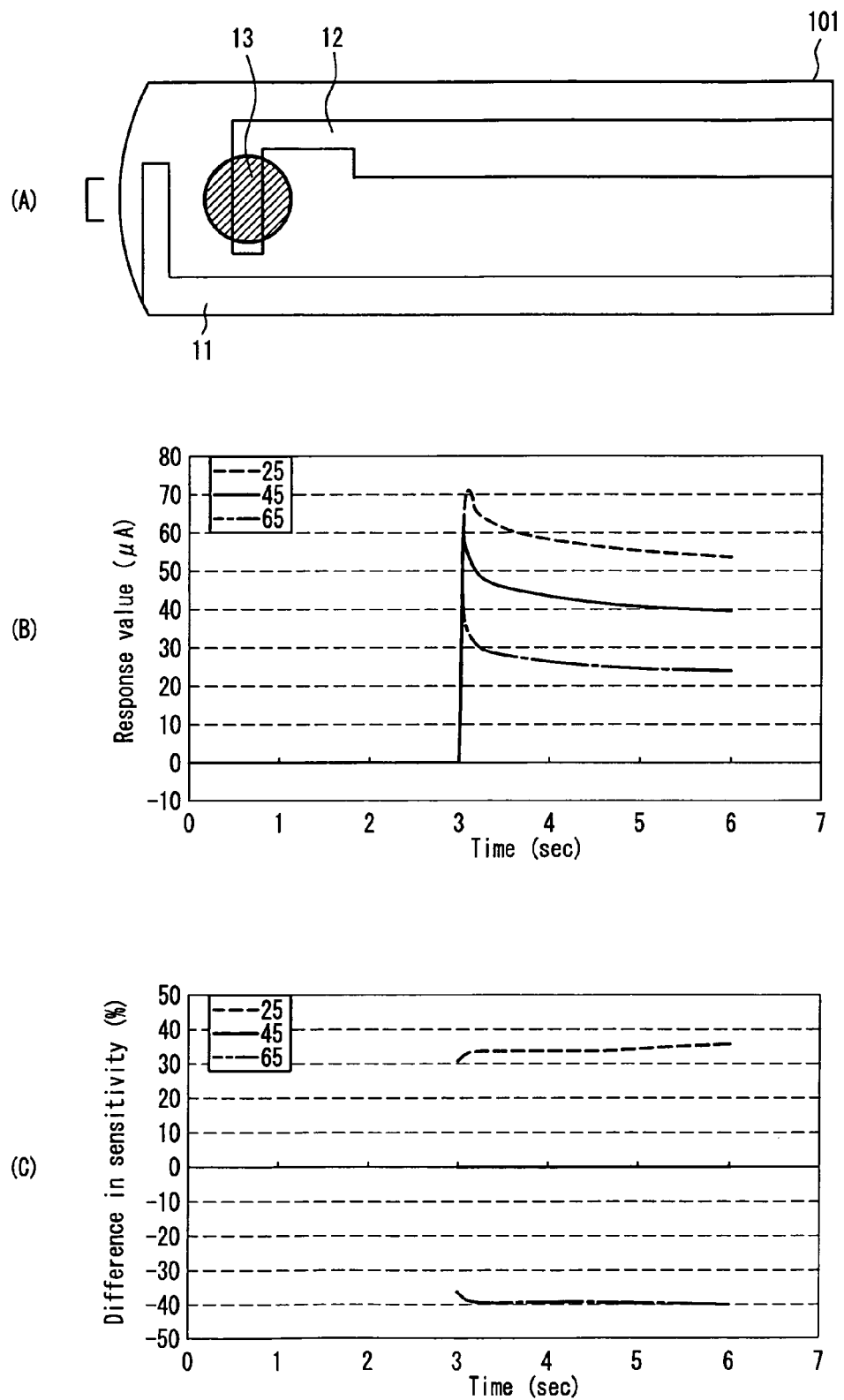
FIG. 10A shows how a redox substance is provided in still another example of a sensor according to the present invention.
FIG. 10B is a graph showing changes in response current (A) over time during voltage application in the example.
FIG. 10C is a graph showing changes in difference in sensitivity (%) over time during the voltage application in the example.
Figure 11:
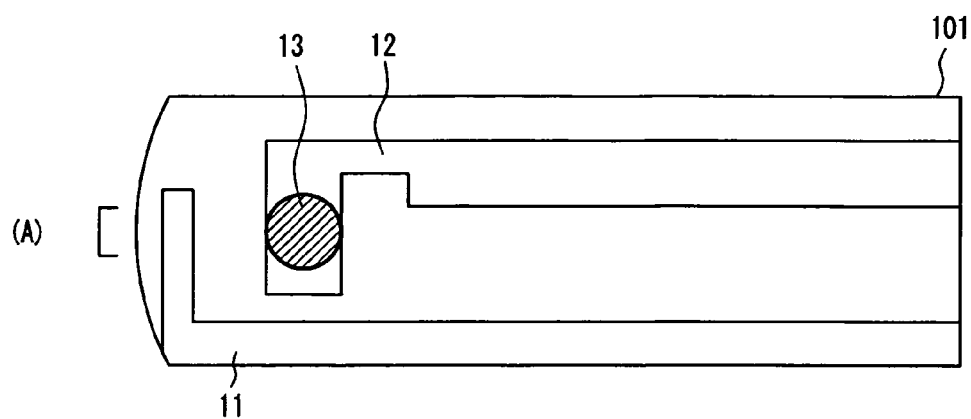
FIG. 11A shows how a redox substance is provided in still another example of a sensor according to the present invention.
FIG. 11B is a graph showing changes in response current (A) over time during voltage application in the example.
FIG. 11C is a graph showing changes in difference in sensitivity (%) over time during the voltage application in the example.
Figure 11:
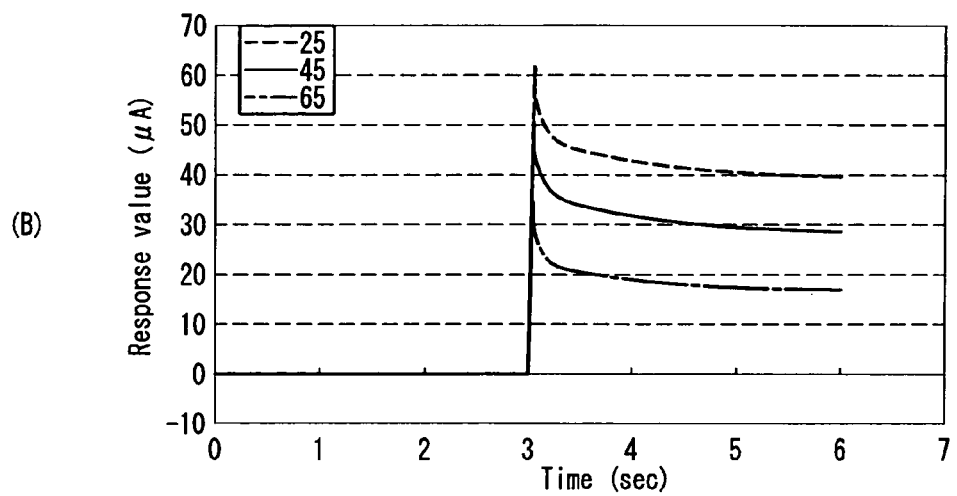
Figure 11:
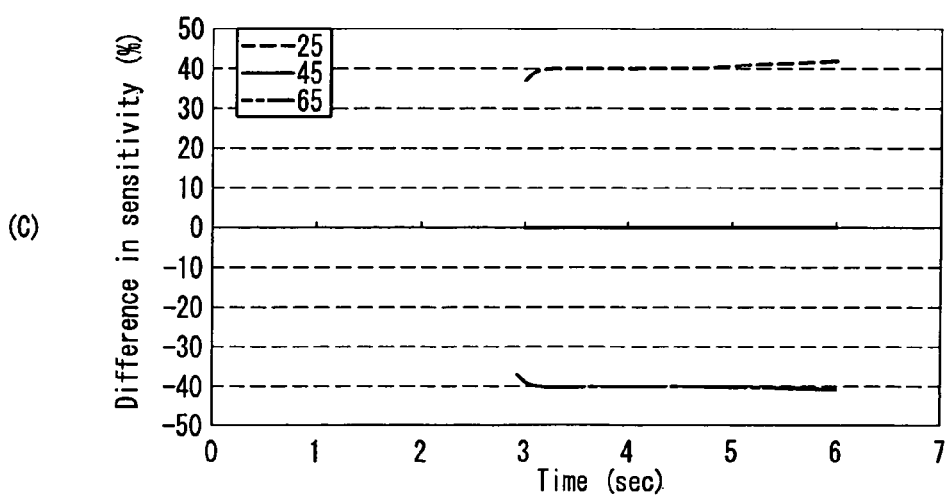
Figure 12:
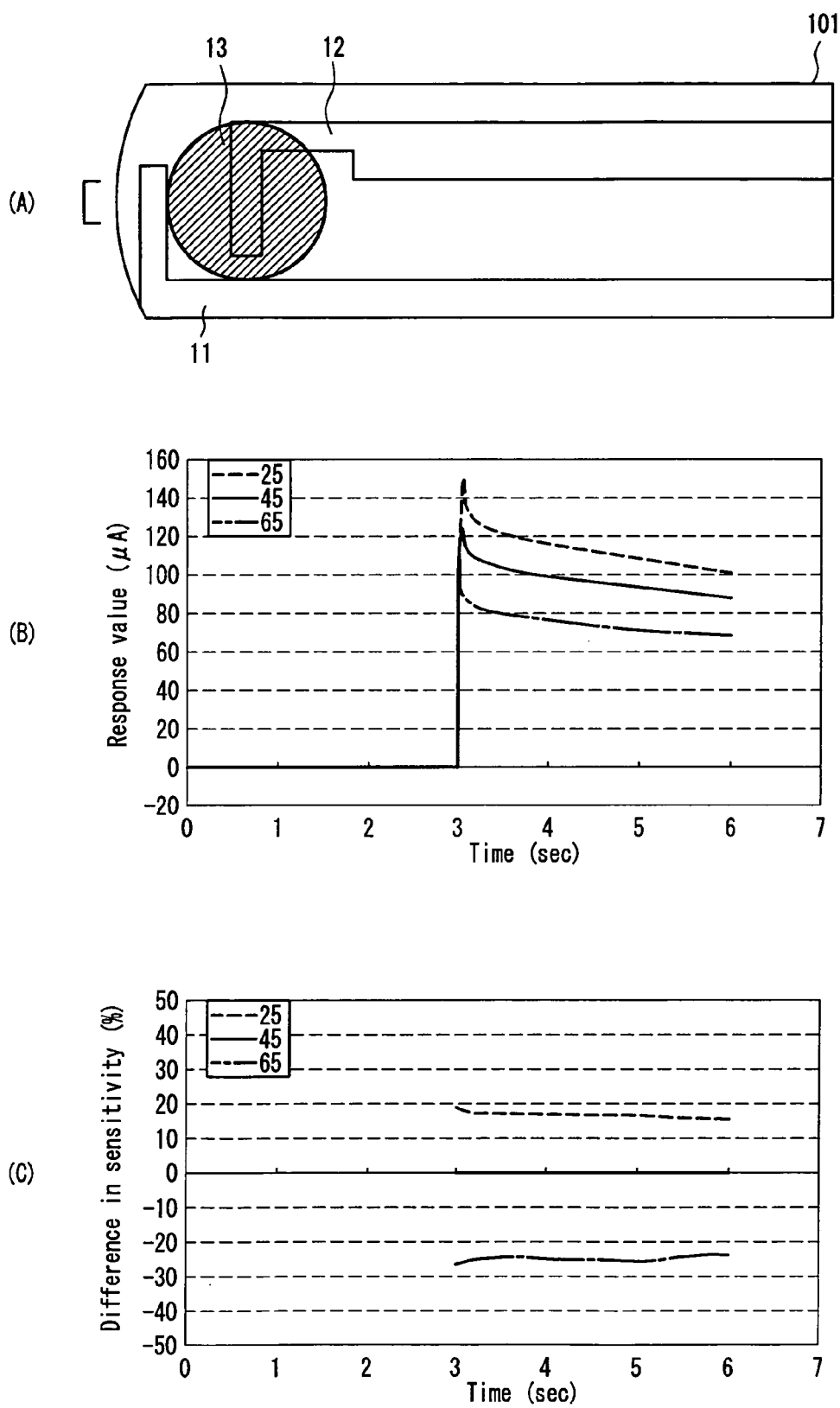
FIG. 12A shows how a redox substance is provided in still another example of a sensor according to the present invention.
FIG. 12B is a graph showing changes in response current (A) over time during voltage application in the example.
FIG. 12C is a graph showing changes in difference in sensitivity (%) over time during the voltage application in the example.
Figure 13:
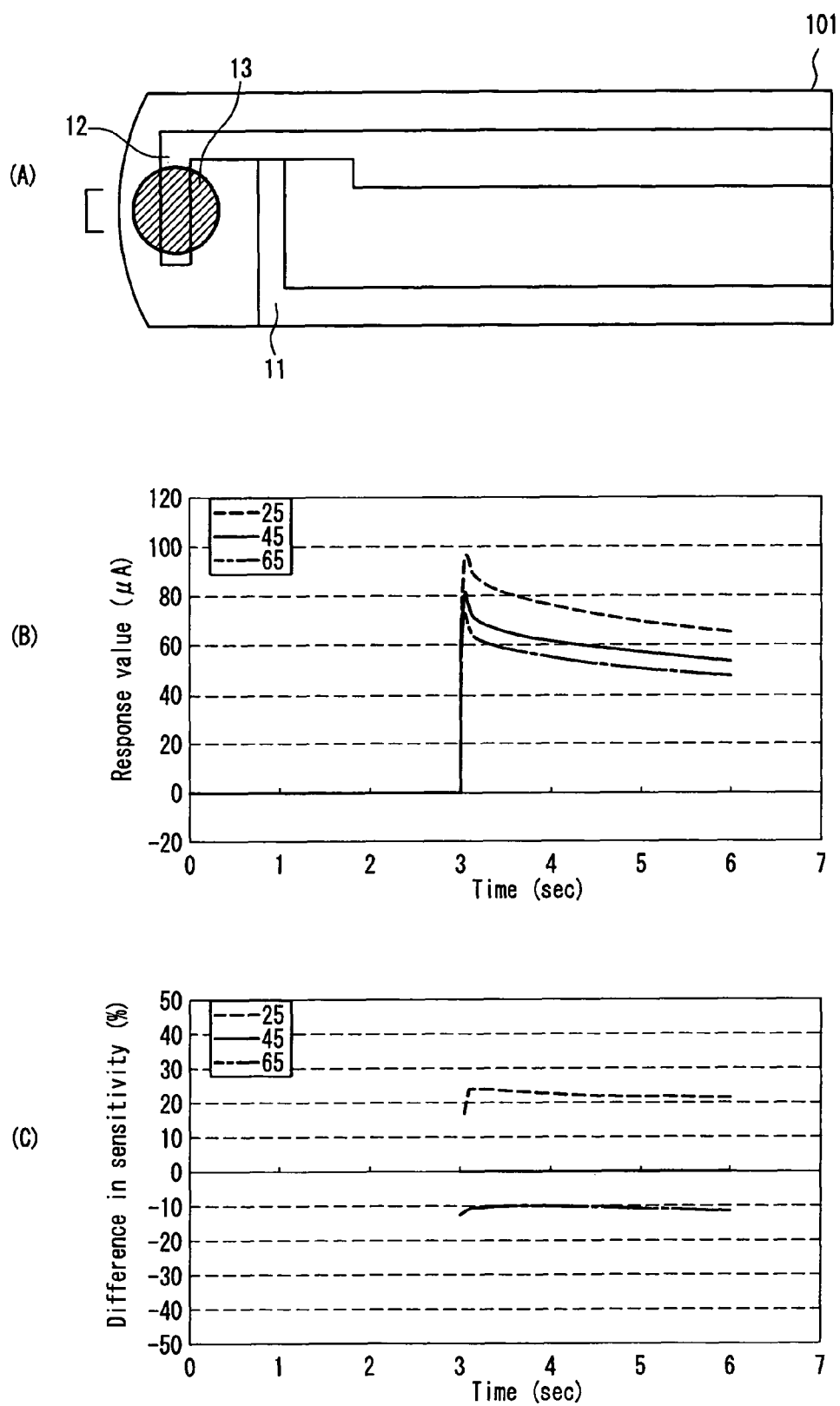
FIG. 13A shows how a redox substance is provided in still another example of a sensor according to the present invention.
FIG. 13B is a graph showing changes in response current (A) over time during voltage application in the example.
FIG. 13C is a graph showing changes in difference in sensitivity (%) over time during the voltage application in the example.
Figure 14:
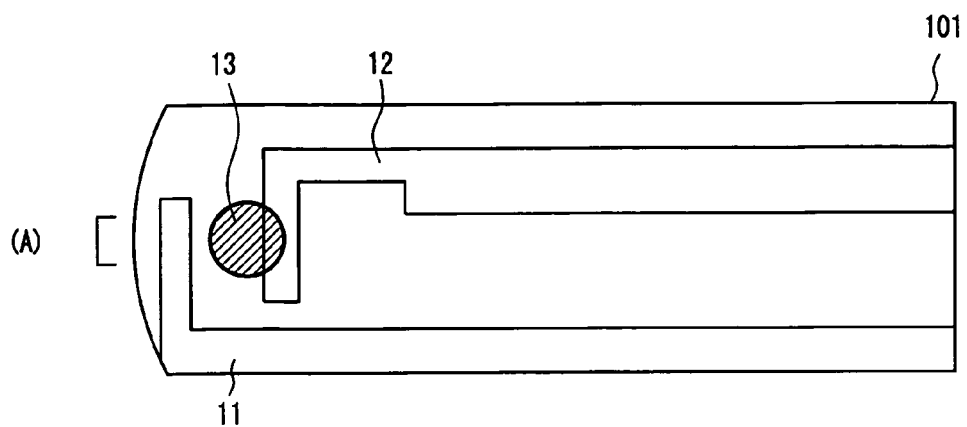
FIG. 14A shows how a redox substance is provided in still another example of a sensor according to the present invention.
FIG. 14B is a graph showing changes in response current (A) over time during voltage application in the example.
FIG. 14C is a graph showing changes in difference in sensitivity (%) over time during the voltage application in the example.
Figure 14:
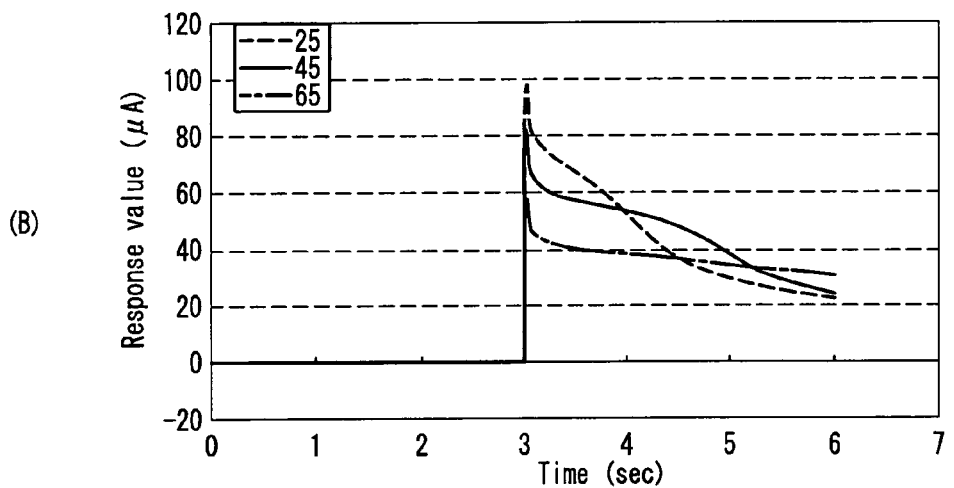
Figure 14:
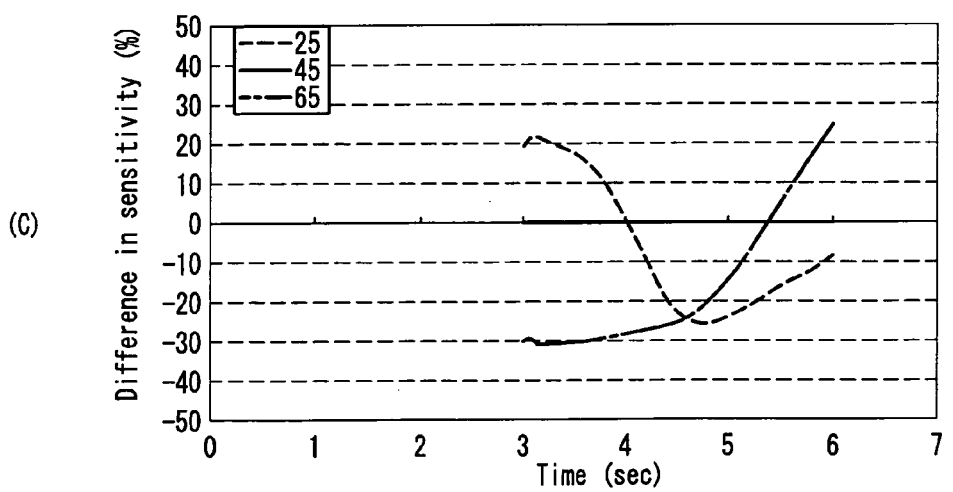
Figure 15:
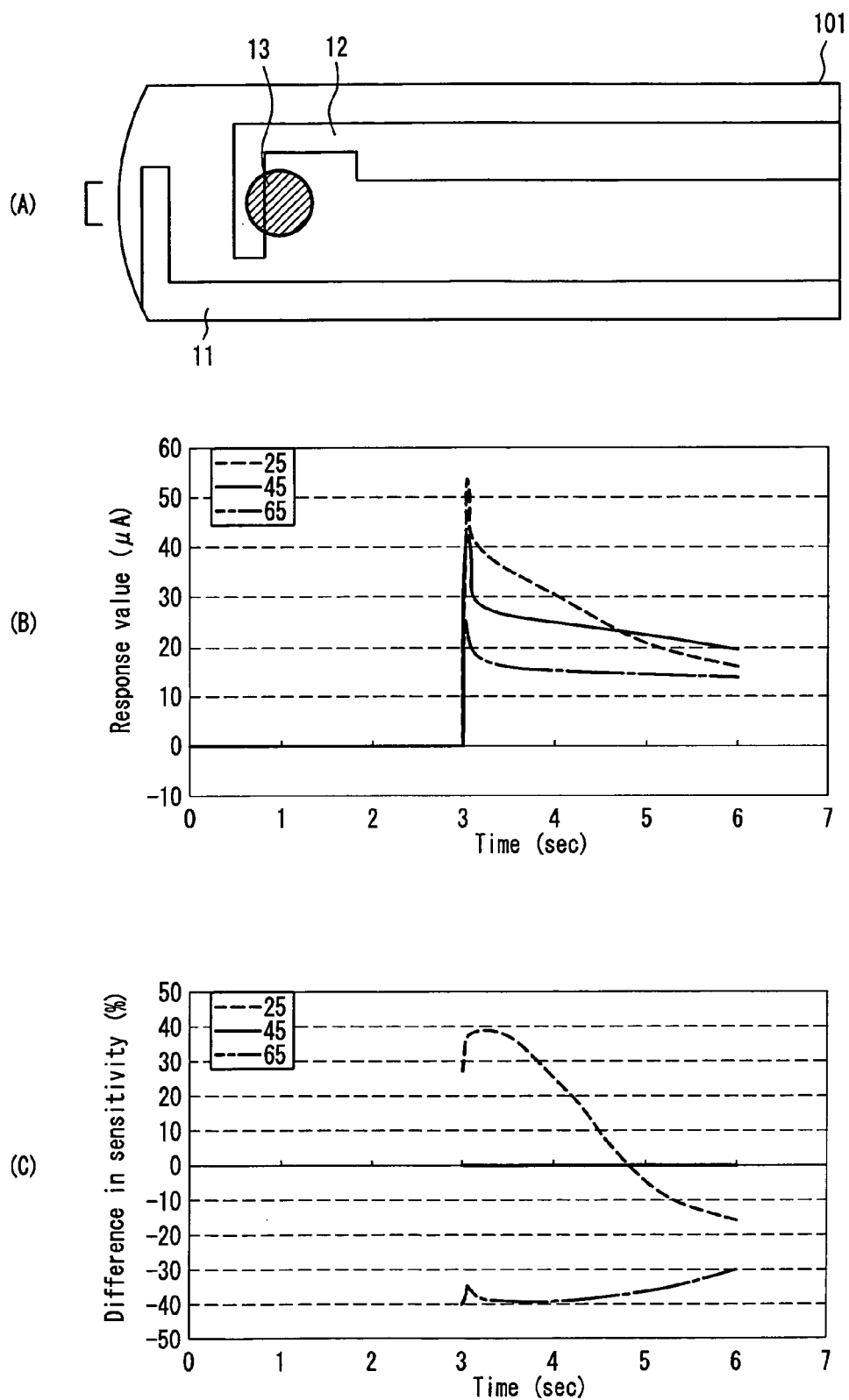
FIG. 15A shows how a redox substance is provided in still another example of a sensor according to the present invention.
FIG. 15B is a graph showing changes in response current (A) over time during voltage application in the example.
FIG. 15C is a graph showing changes in difference in sensitivity (%) over time during the voltage application in the example.
Figure 16:
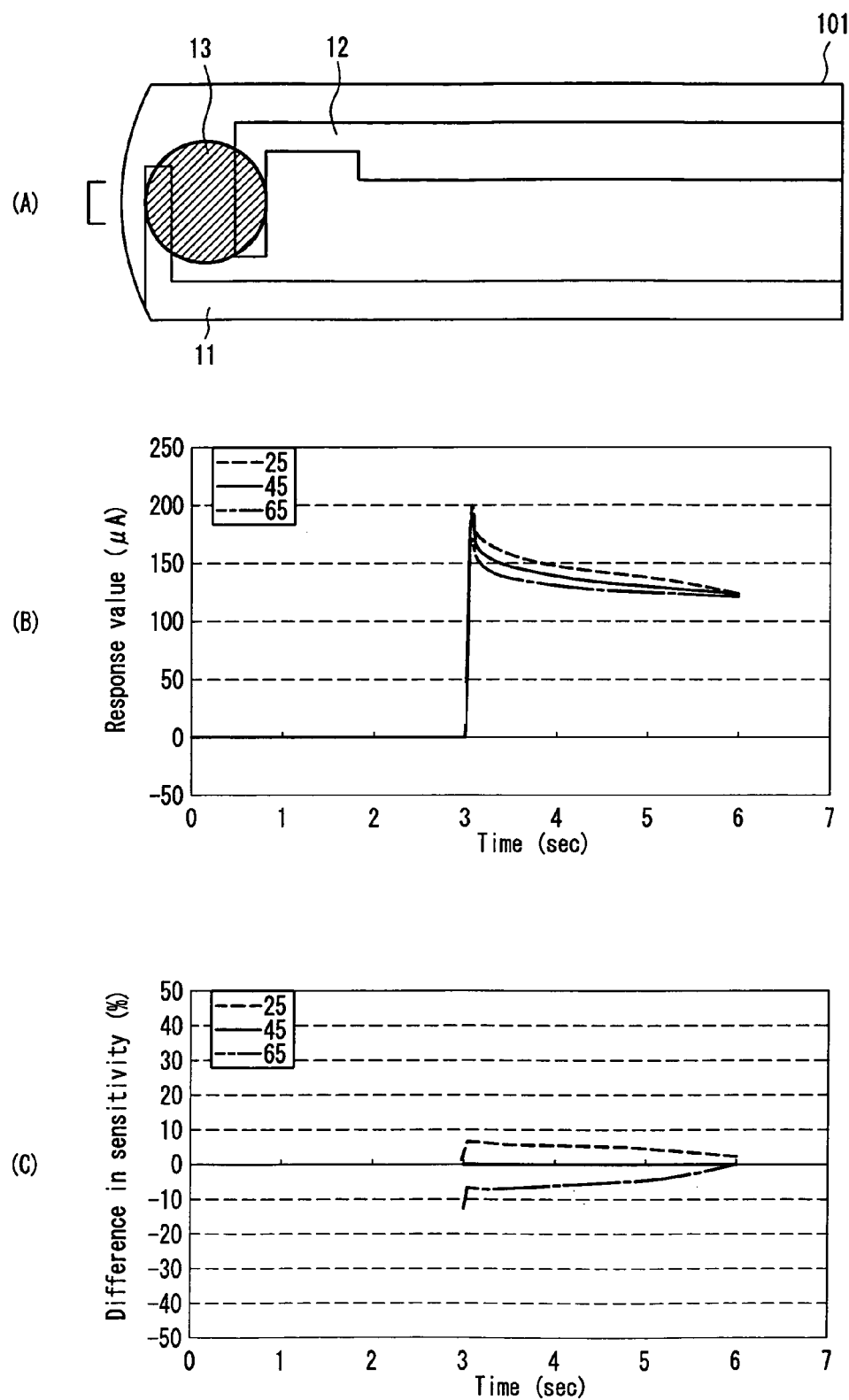
FIG. 16A shows how a redox substance is provided in a sensor according to still another comparative example.
FIG. 16B is a graph showing changes in response current (A) over time during voltage application in the comparative example.
FIG. 16C is a graph showing changes in difference in sensitivity (%) over time during the voltage application in the comparative example.
Figure 17:
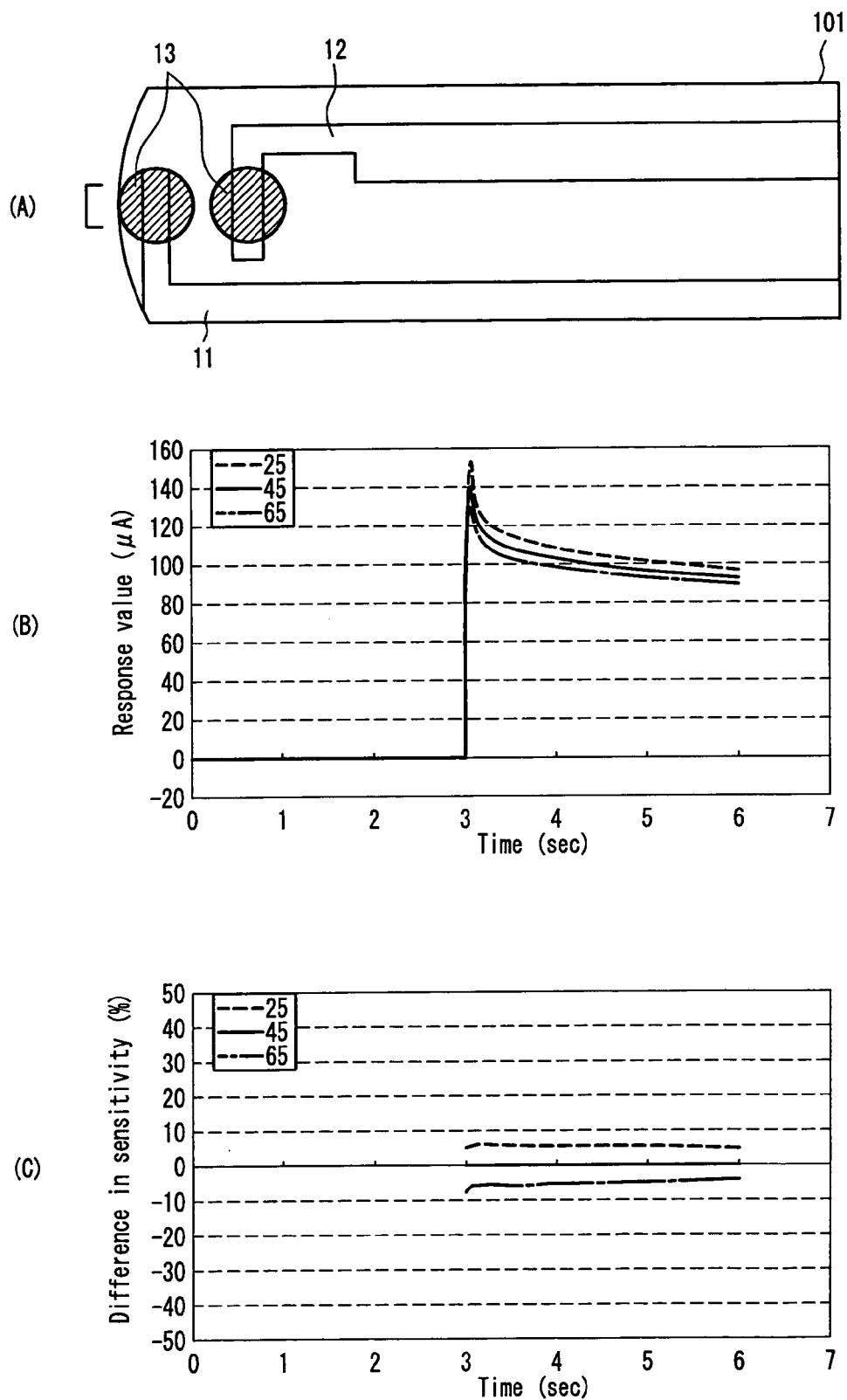
FIG. 17A shows how a redox substance is provided in a sensor according to still another comparative example.
FIG. 17B is a graph showing changes in response current (A) over time during voltage application in the comparative example.
FIG. 17C is a graph showing changes in difference in sensitivity (%) over time during the voltage application in the comparative example.
Figure 18:
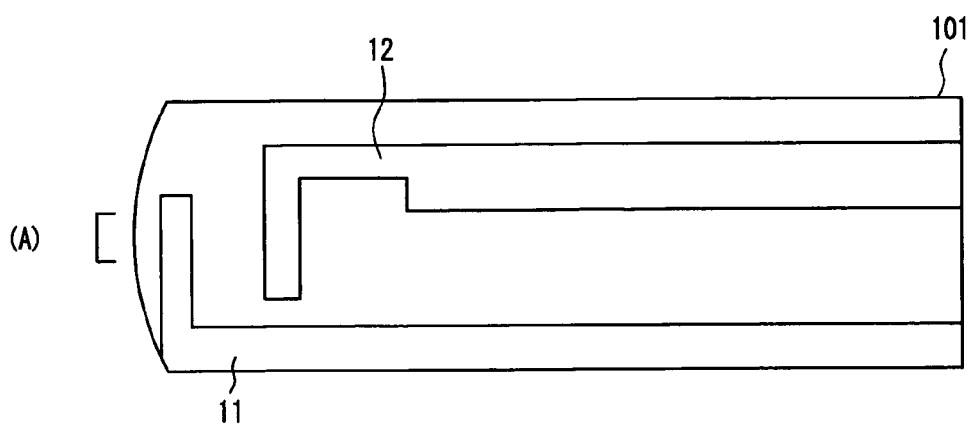
FIG. 18A shows how a redox substance is provided in a sensor according to still another comparative example.
FIG. 18B is a graph showing changes in response current (A) over time during voltage application in the comparative example.
FIG. 18C is a graph showing changes in difference in sensitivity (%) over time during the voltage application in the comparative example.
Figure 18:
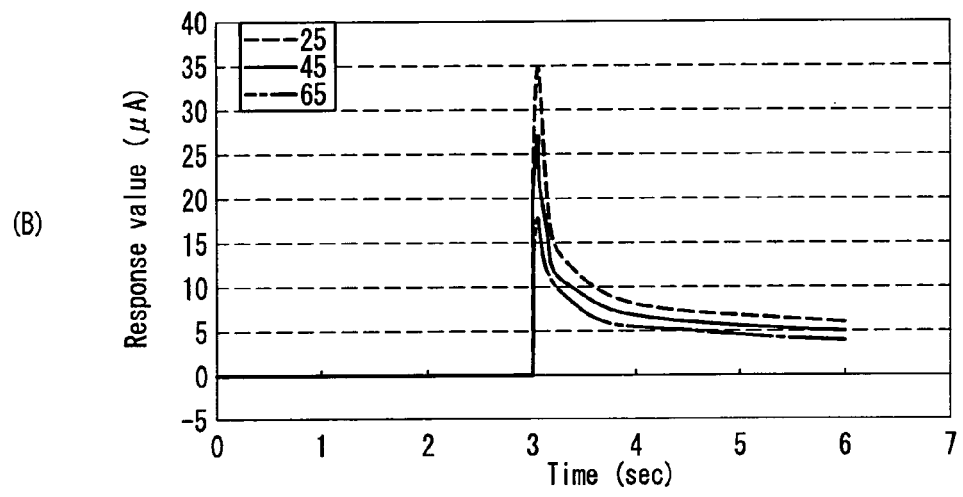
Figure 18:
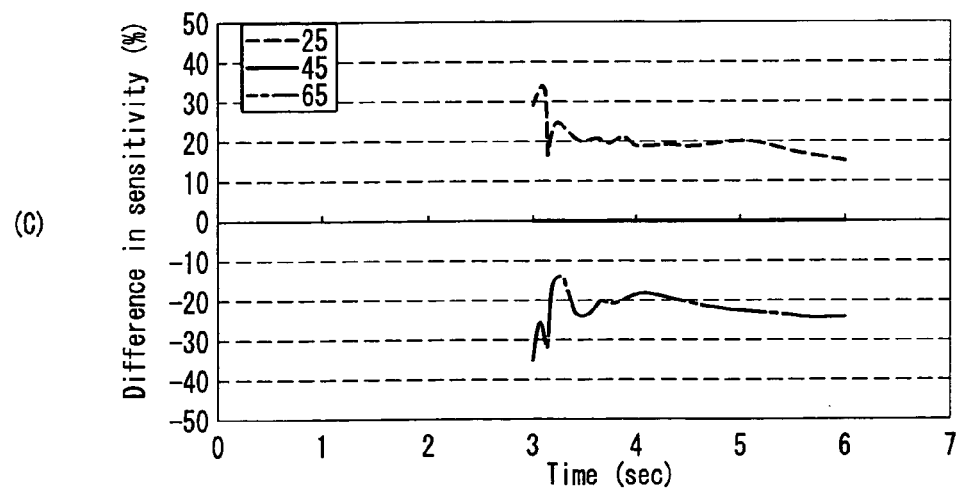

A sensor was produced in the same manner as in Comparative Example 1, except that a reagent solution was prepared by dissolving, in a 0.01 to 2.0 wt % CMC aqueous solution, potassium ferricyanide so that its concentration became 10 to 200 mM and taurine so that its concentration became 10 to 300 mM and this reagent solution was dropped on the working electrode 31 and the counter electrode 32 on the substrate so that the droplet of the reagent solution extended to the outside of the electrodes and then dried. Except for the above, the current flowing between the electrodes of the sensor was measured under the same measurement conditions as in Example 1 (e.g., the applied voltage was 2.5 V) with regard to the above-noted three samples having the different Hct values. The results are shown in the graphs of FIGS. 9B and 9C. FIG. 9B is a graph showing changes in response current (μA) over time during the application of the voltage (V); and FIG. 9C is a graph showing changes in difference in sensitivity (%) over time during the application of the voltage (V). As shown in FIGS. 9B and 9C, in this comparative example, the difference in sensitivity was greatly affected by the voltage application time, so that the response current suitable for quantifying a Hct could not be obtained.

Example 2

In the present example, six types of sensors (2-1 to 2-6) were produced so that they were different from each other in the arrangement of a redox substance (potassium ferricyanide) with respect to a working electrode or a counter electrode, and the response current and the difference in sensitivity were measured using these sensors. Also, as sensors according to Comparative Example 3, three types of sensors (2-7 to 2-9) were produced so that they were different from each other in the arrangement of a redox substance (potassium ferricyanide) with respect to a working electrode or a counter electrode, and the response current and the difference in sensitivity were measured using these sensors. Note here that the above-described respective sensors were produced in the same manner as in Example 1 except for the arrangement of the redox substance and the distance between the electrodes (1.15 mm). Also note that the response current and the difference in sensitivity were measured in the same manner as in Example 1. The arrangement pattern of the redox substance in each of the sensor and the results of the measurement will be described in the following. In FIGS. 10 to 18, FIGS. 10A to 18A show an arrangement pattern of the redox substance, FIGS. 10B to 18B are graphs each showing changes in response current (A) over time during the application of the voltage (V), and FIGS. 10C to 18C are graphs each showing changes in difference in sensitivity (%) over time during the application of the voltage (V).

(2-1)

As shown in FIG. 10A, in the sensor of this example, the redox substance 13 was provided so as to extend to the outside of the counter electrode 12, so that the redox substance 13 was present on the surface of the counter electrode 12 and at a portion on the counter electrode side between the electrodes. The graphs of FIGS. 10B and 10C show the results of the measurement of the current flowing between the electrodes of this sensor. As shown in FIGS. 10B and 10C, according to this sensor, the difference in sensitivity did not depend on the voltage application time, so that the response current reflecting the Hct value could be detected definitely and favorably.

(2-2)

As shown in FIG. 11A, in the sensor of this example, the redox substance 13 was provided only on the surface of the counter electrode 12. The graphs of FIGS. 11B and 11C show the results of the measurement of the current flowing between the electrodes of this sensor. As shown in FIGS. 11B and 11C, according to this sensor, the difference in sensitivity did not depend on the voltage application time, so that the response current reflecting the Hct value could be detected definitely and favorably.

(2-3)

As shown in FIG. 12A, in the sensor of this example, the redox substance 13 was provided so as to extend to the outside of the counter electrode 12, so that the redox substance was present on the surface of the counter electrode 12 and between the electrodes. Note here that no redox substance was present on the working electrode 11. The graphs of FIGS. 12B and 12C show the results of the measurement of the current flowing between the electrodes of this sensor. As shown in FIGS. 12B and 12C, according to this sensor, the difference in sensitivity did not depend on the voltage application time, so that the response current reflecting the Hct value could be detected definitely.

(2-4)

As shown in FIG. 13A, in the sensor of this example, the positions of the working electrode 11 and the counter electrode 12 were switched so that the counter electrode 12 on which the redox substance 13 was provided was on an upstream side and the working electrode 11 on which the redox substance 13 was not provided was on a downstream side with respect to the flow of blood supplied to the sensor. The graphs of FIGS. 13B and 13C show the results of the measurement of the current flowing between the electrodes of this sensor. As shown in FIGS. 13B and 13C, according to this sensor, the difference in sensitivity did not depend on the voltage application time, so that the response current reflecting the Hct value could be detected definitely. However, the difference in sensitivity was slightly smaller than those exhibited by the sensors according to the examples (2-1), (2-2), and (2-3).

(2-5)

As shown in FIG. 14A, in the sensor of this example, the redox substance 13 was provided so as to extend to the outside of the counter electrode 12, so that the redox substance 13 was present on a part of the surface of the counter electrode 12 and at a portion on the counter electrode side between the electrodes. The graphs of FIGS. 14B and 14C show the results of the measurement of the current flowing between the electrodes of this sensor. As shown in FIGS. 14B and 14C, according to this sensor, for one second immediately after the start of the voltage application i.e., one second between third to fourth seconds in the drawings), the difference in sensitivity did not depend on the voltage application time so that the response current reflecting the Hct value could be detected definitely.

(2-6)

As shown in FIG. 15A, in the sensor of this example, the redox substance 13 was provided so as to extend to the outside of the counter electrode 12, so that the redox substance was present on a part of the surface of the counter electrode 12. Note here that the redox substance was not present between the electrodes. The graphs of FIGS. 15B and 15C show the results of the measurement of the current flowing between the electrodes of this sensor. As shown in FIGS. 15B and 15C, according to this sensor, for one second immediately after the start of the voltage application (i.e., one second between third to fourth seconds in the drawings), the difference in sensitivity did not depend on the voltage application time so that the response current reflecting the Hct value could be detected definitely.

(2-7)

As shown in FIG. 16A, in the sensor of this comparative example, the redox substance 13 was provided so as to lie over the working electrode 11, the counter electrode 12, and both the electrodes. The graphs of FIGS. 16B and 16C show the results of the measurement of the current flowing between the electrodes of this sensor. As shown in FIGS. 16B and 16C, according to this sensor, the response current reflecting the Hct value could not be detected definitely.

(2-8)

As shown in FIG. 17A, in the sensor of this comparative example, the redox substances 13 were provided so as to lie over the working electrode 11, the counter electrode 12, and a part of both the electrodes. The graphs of FIGS. 17B and 17C show the results of the measurement of the current flowing between the electrodes of this sensor. As shown in FIGS. 17B and 17C, according to this sensor, the response current reflecting the Hct value could not be detected definitely.

(2-9)

As shown in FIG. 18A, in the sensor of this comparative example, the redox substance 13 was not provided. The graphs of FIGS. 18B and 18C shows the results of the measurement of the current flowing between the electrodes of this sensor. As shown in FIGS. 18B and 18C, according to this sensor, the response current reflecting the Hct value could not be detected.

Example 3

In the present example, the response current and the difference in sensitivity of a sensor were measured at various applied voltages in the range from 0.5 to 6.5 V. The sensor was produced in the same manner as in Example 1. Furthermore, the response current and the difference in sensitivity were measured in the same manner as in Example 1. The results of the measurement are shown in the graphs of FIGS. 19 to 31. In FIGS. 19 to FIG. 31, FIGS. 19A to 31A are graphs each showing changes in response current (A) over time during the application of the voltage (V), and FIGS. 19B to 31B are graphs each showing changes in difference in sensitivity (%) over time during the application of the voltage (V).

Figure 19:
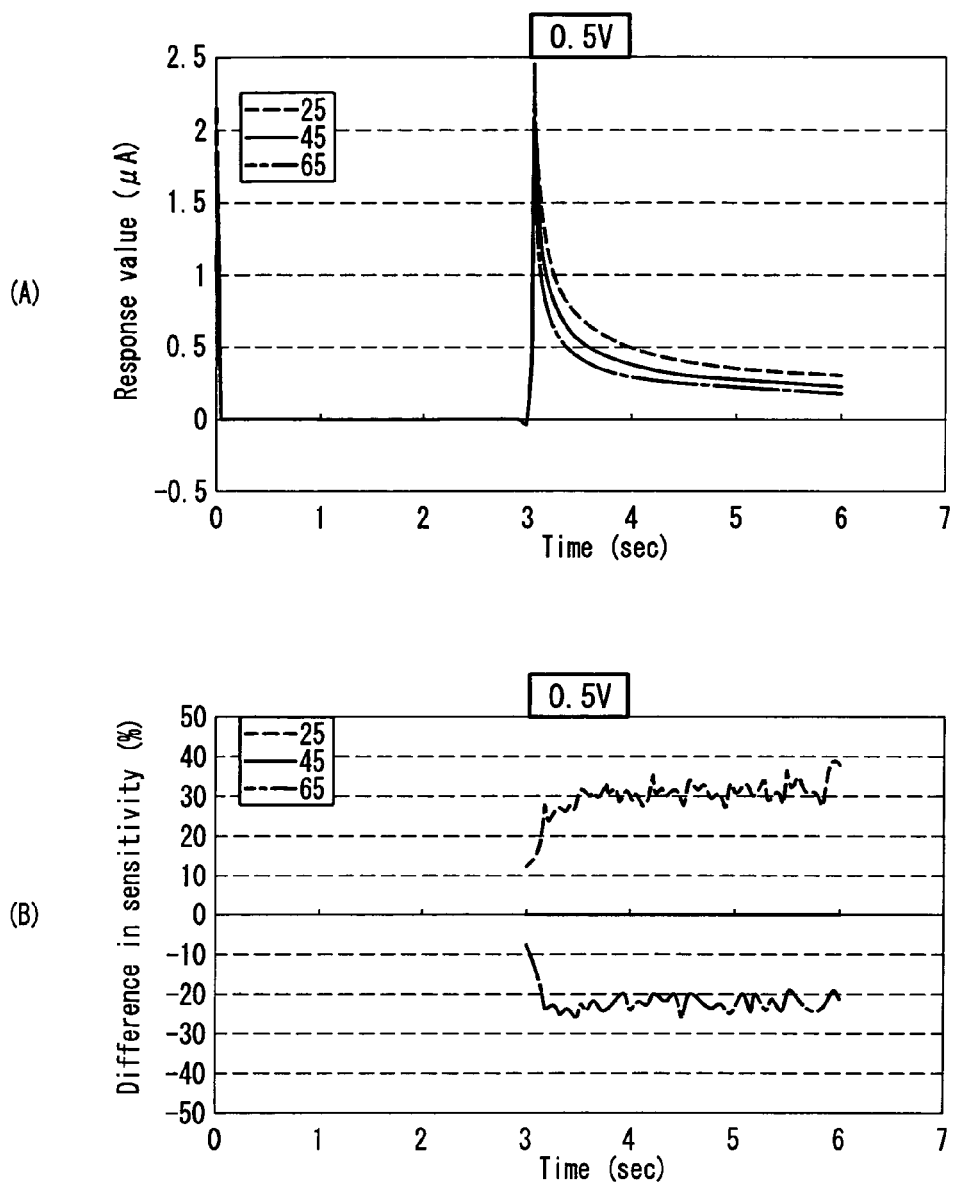
FIG. 19A is a graph showing changes in response current (A) over time during voltage application (0.5 V) in still another example of a sensor according to the present invention.
FIG. 19B is a graph showing changes in difference in sensitivity (%) over time during the voltage application in the example.
Figure 20:
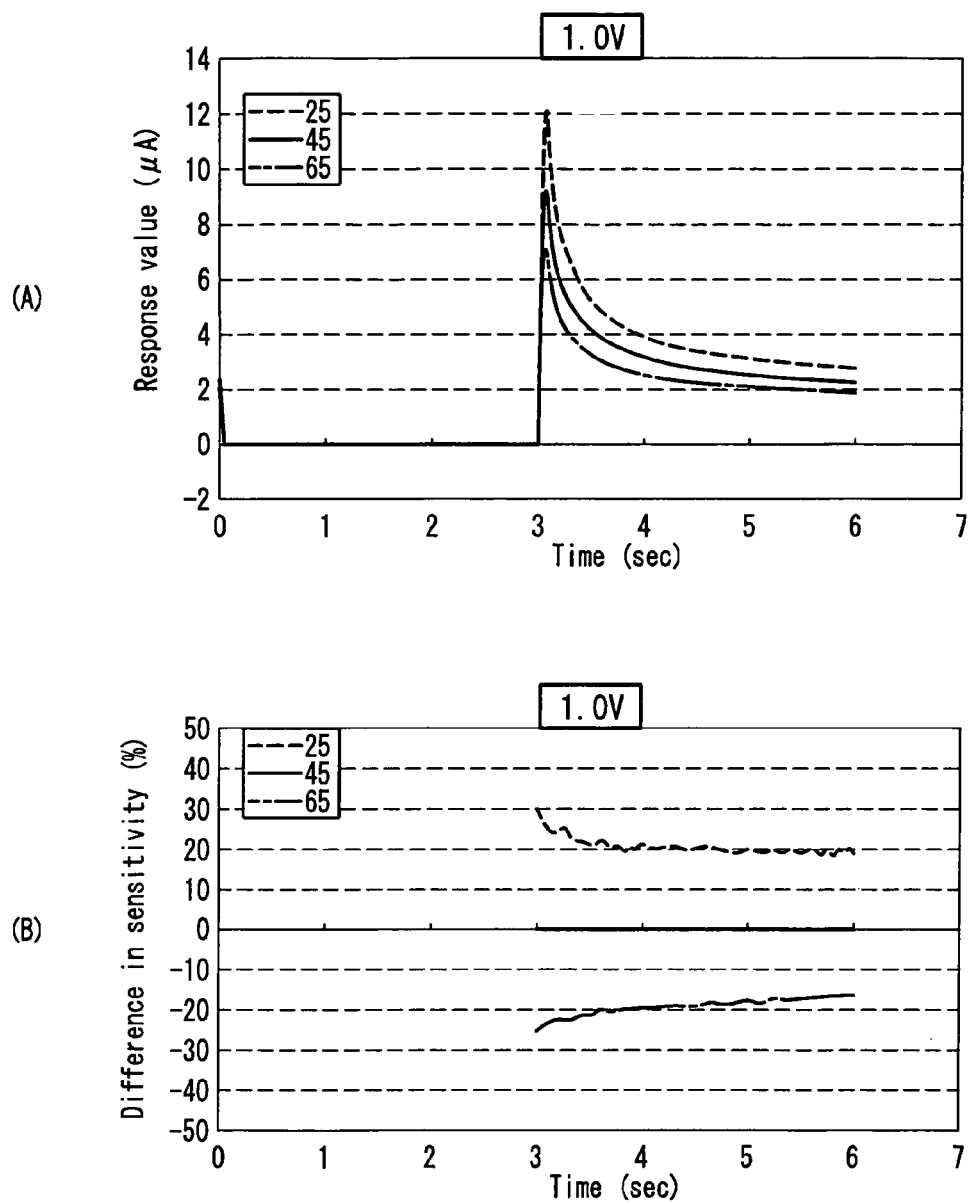
FIG. 20A is a graph showing changes in response current (A) over time during voltage application (1.0 V) in still another example of a sensor according to the present invention.
FIG. 20B is a graph showing changes in difference in sensitivity (%) over time during the voltage application in the example.
Figure 21:
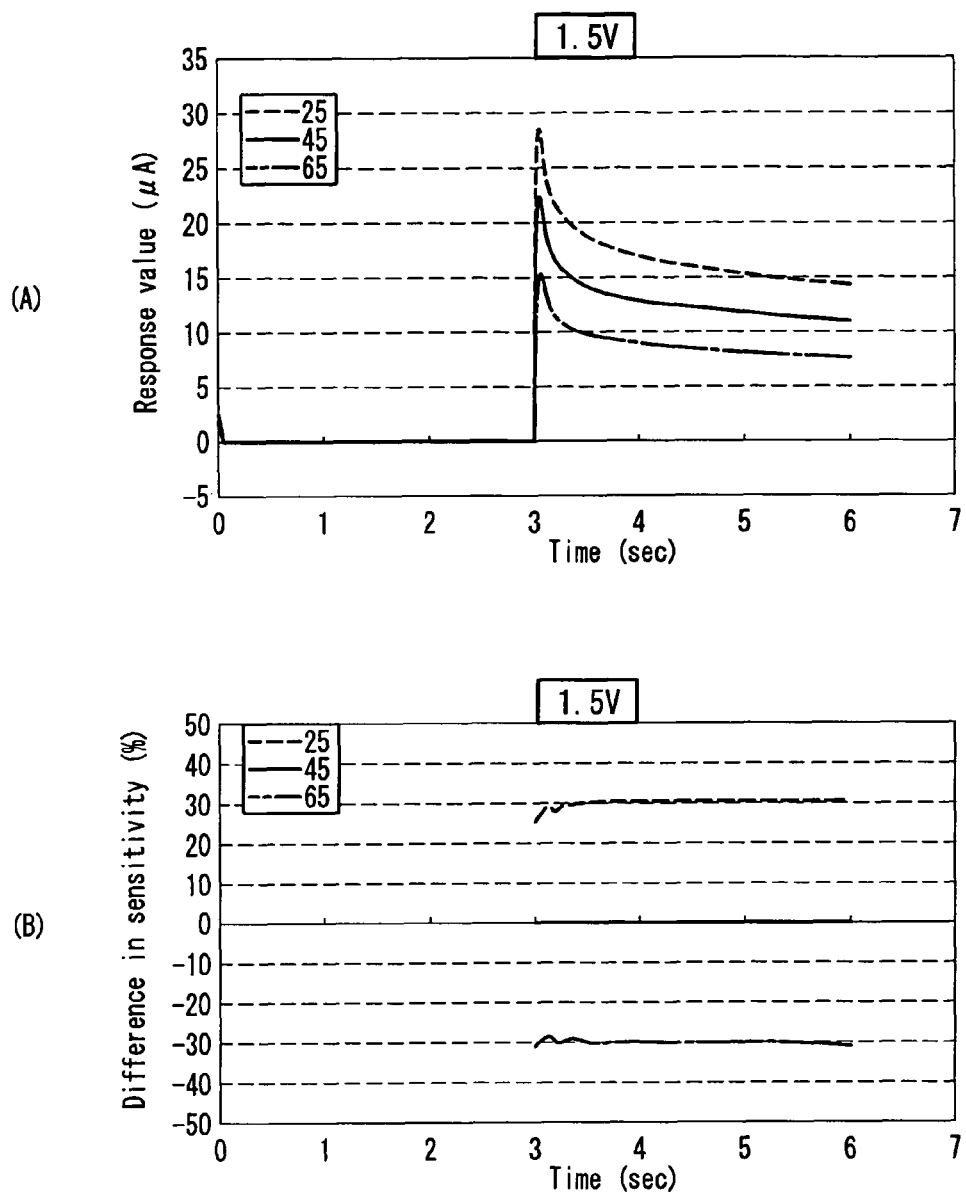
FIG. 21A is a graph showing changes in response current (A) over time during voltage application (1.5 V) in still another example of a sensor according to the present invention.
FIG. 21B is a graph showing changes in difference in sensitivity (%) over time during the voltage application in the example.
Figure 22:
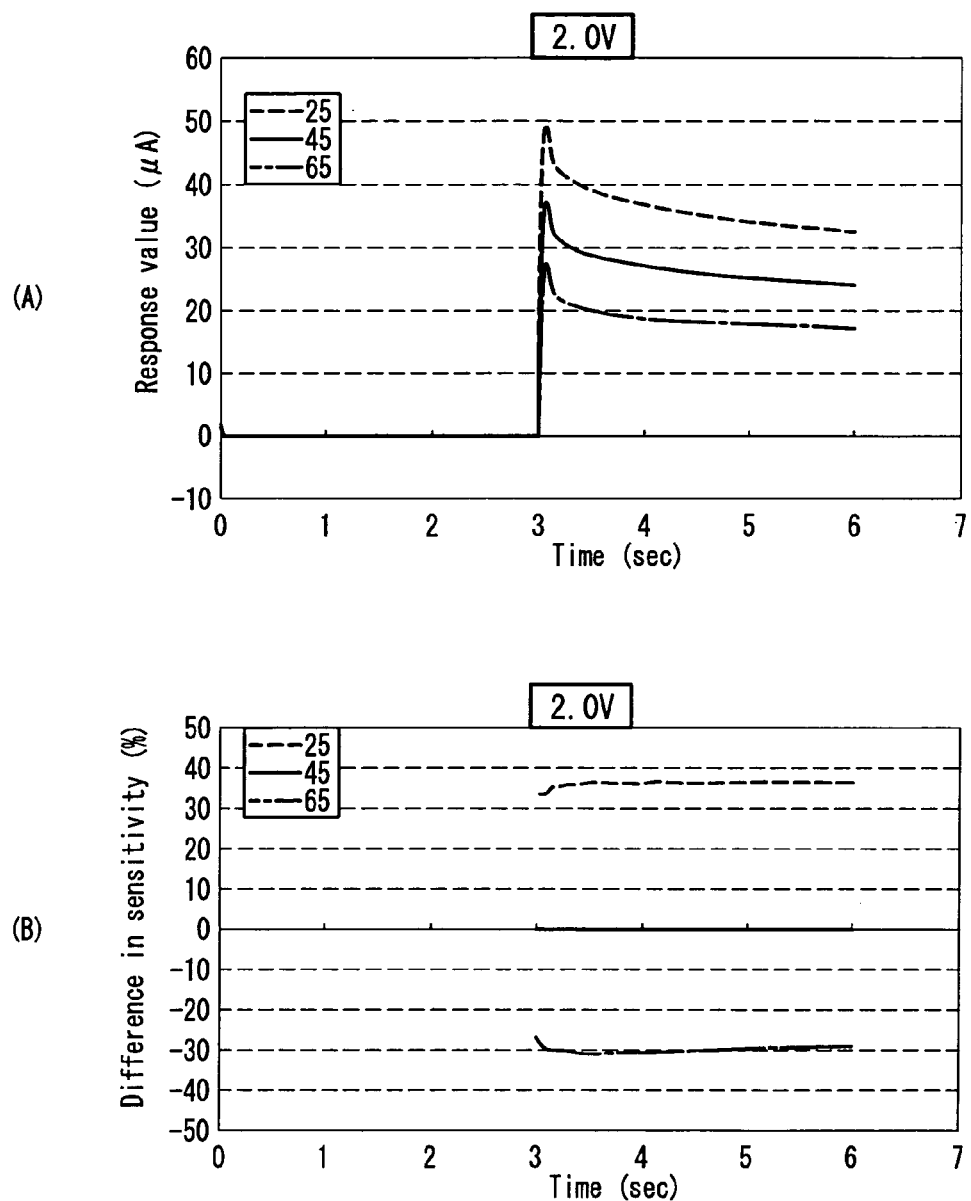
FIG. 22A is a graph showing changes in response current (A) over time during voltage application (2.0 V) in still another example of a sensor according to the present invention.
FIG. 22B is a graph showing changes in difference in sensitivity (%) over time during the voltage application in the example.
Figure 23:
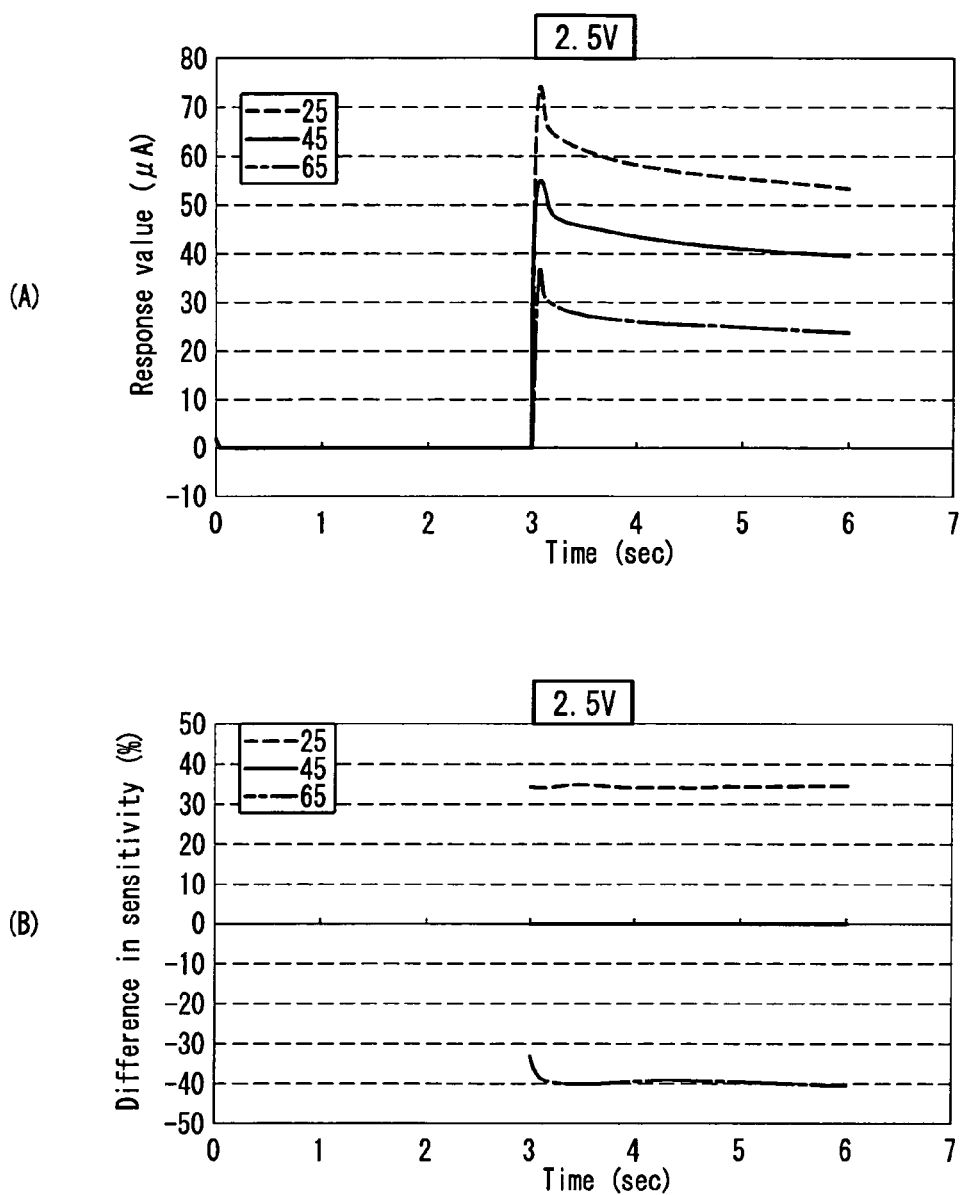
FIG. 23A is a graph showing changes in response current (A) over time during voltage application (2.5 V) in still another example of a sensor according to the present invention.
FIG. 23B is a graph showing changes in difference in sensitivity (%) over time during the voltage application in the example.
Figure 24:
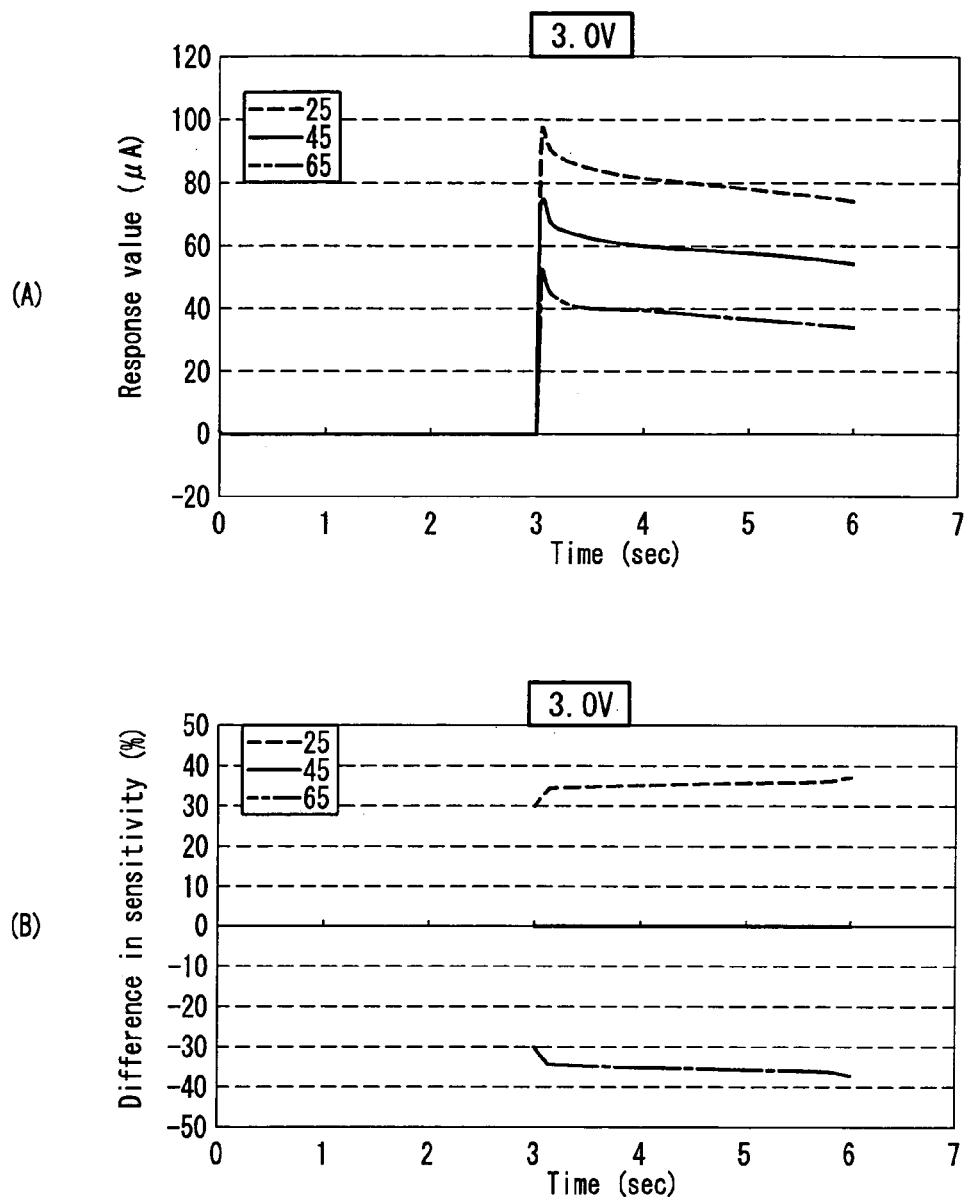
FIG. 24A is a graph showing changes in response current (A) over time during voltage application (3.0 V) in still another example of a sensor according to the present invention.
FIG. 24B is a graph showing changes in difference in sensitivity (%) over time during the voltage application in the example.
Figure 25:
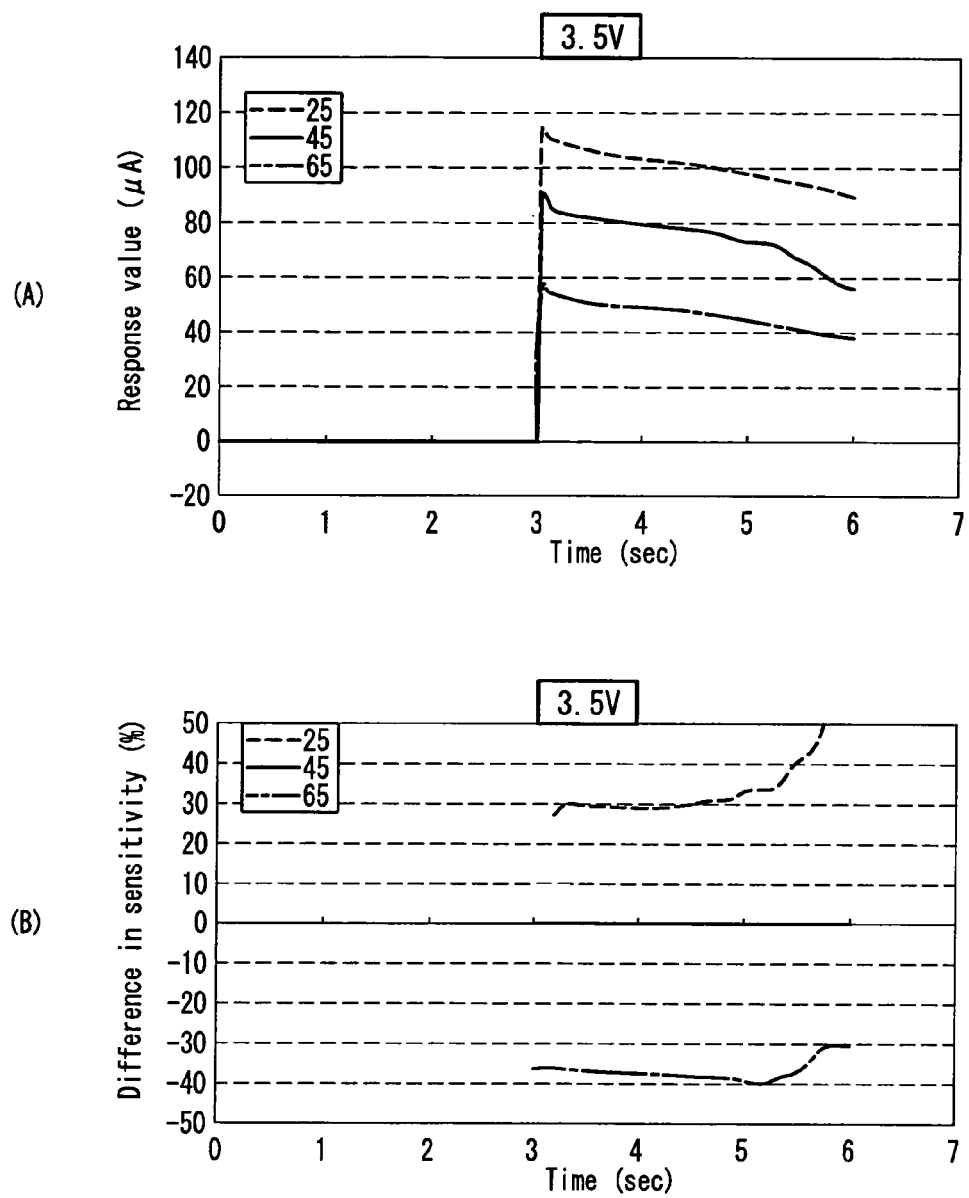
FIG. 25A is a graph showing changes in response current (A) over time during voltage application (3.5 V) in still another example of a sensor according to the present invention.
FIG. 25B is a graph showing changes in difference in sensitivity (%) over time during the voltage application in the example.
Figure 26:
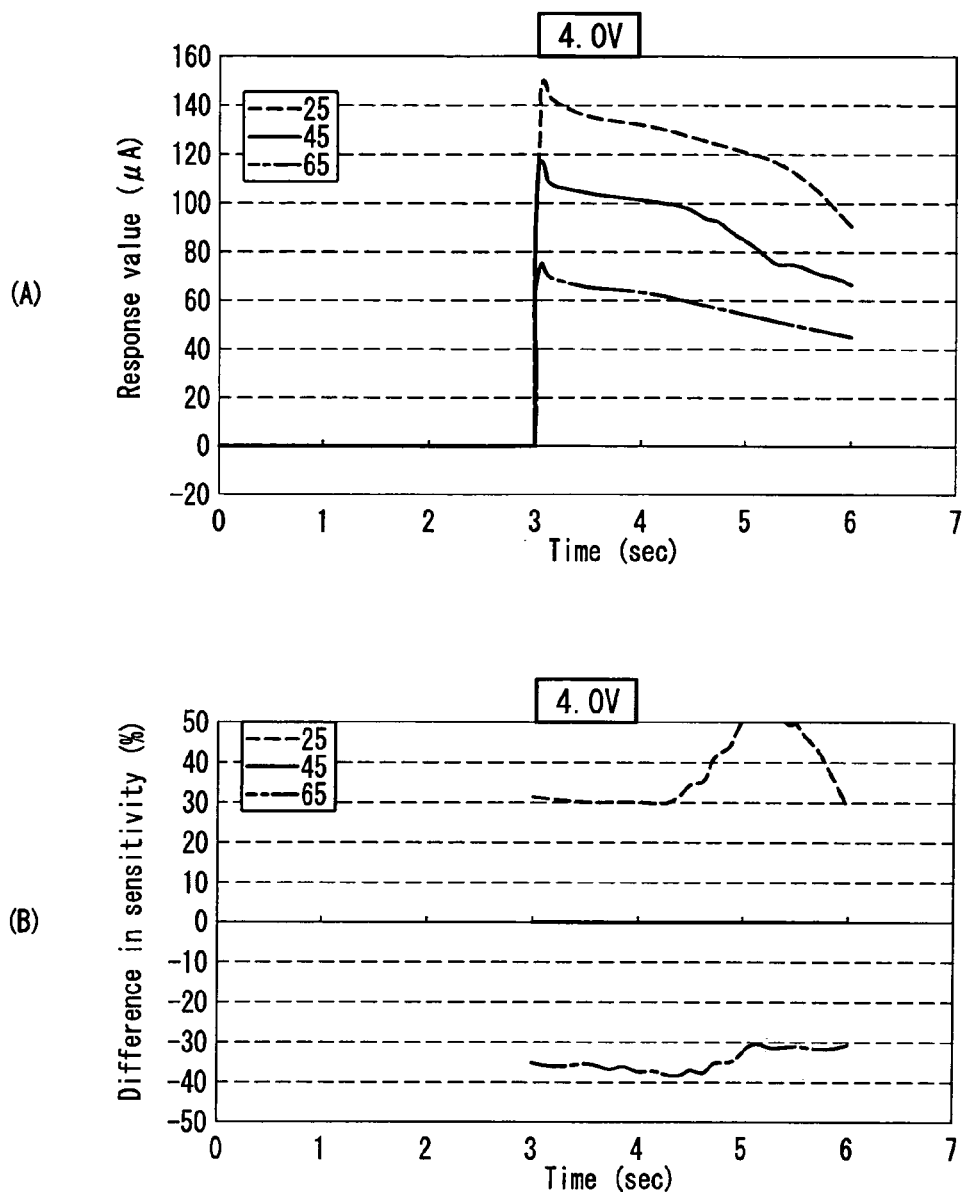
FIG. 26A is a graph showing changes in response current (A) over time during voltage application (4.0 V) in still another example of a sensor according to the present invention.
FIG. 26B is a graph showing changes in difference in sensitivity (%) over time during the voltage application in the example.
Figure 27:
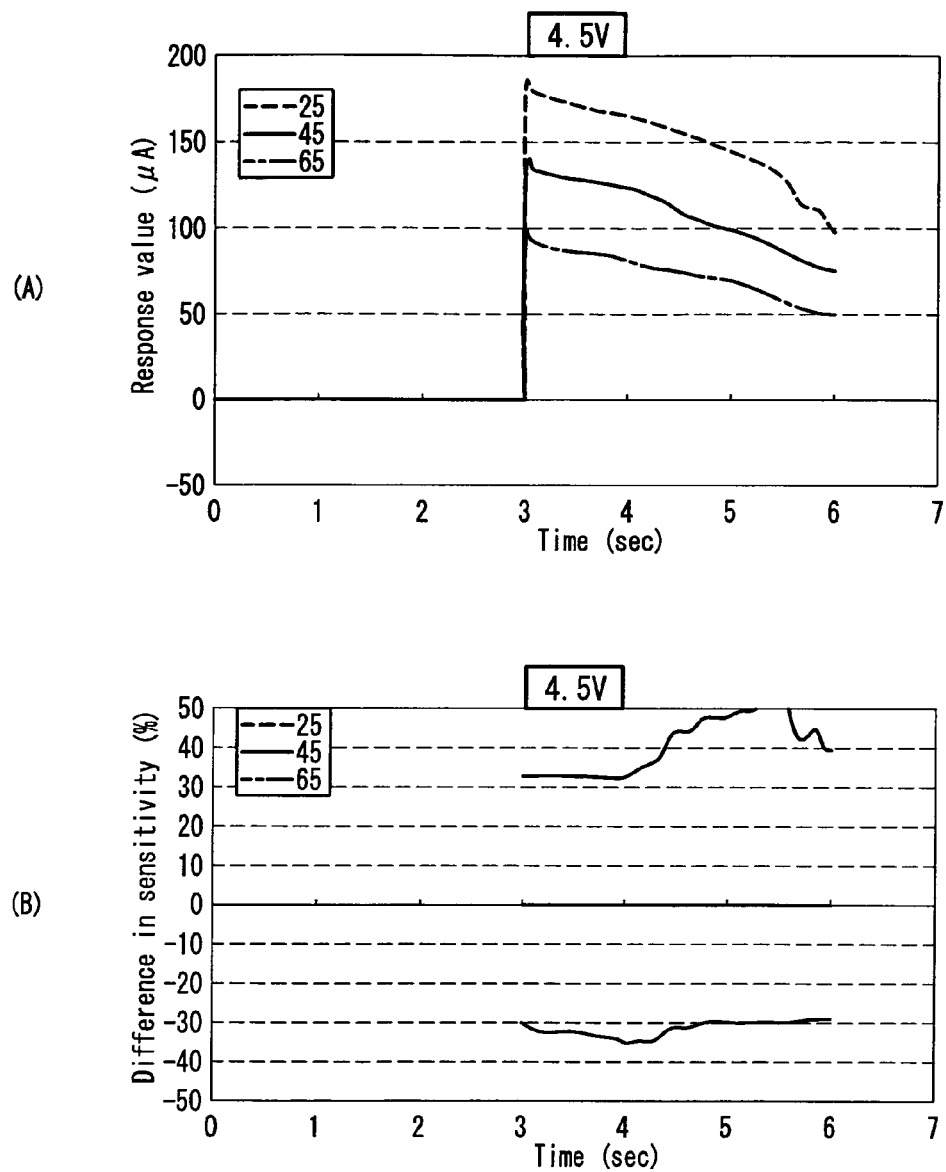
FIG. 27A is a graph showing changes in response current (A) over time during voltage application (4.5 V) in still another example of a sensor according to the present invention.
FIG. 27B is a graph showing changes in difference in sensitivity (%) over time during the voltage application in the example.
Figure 28:
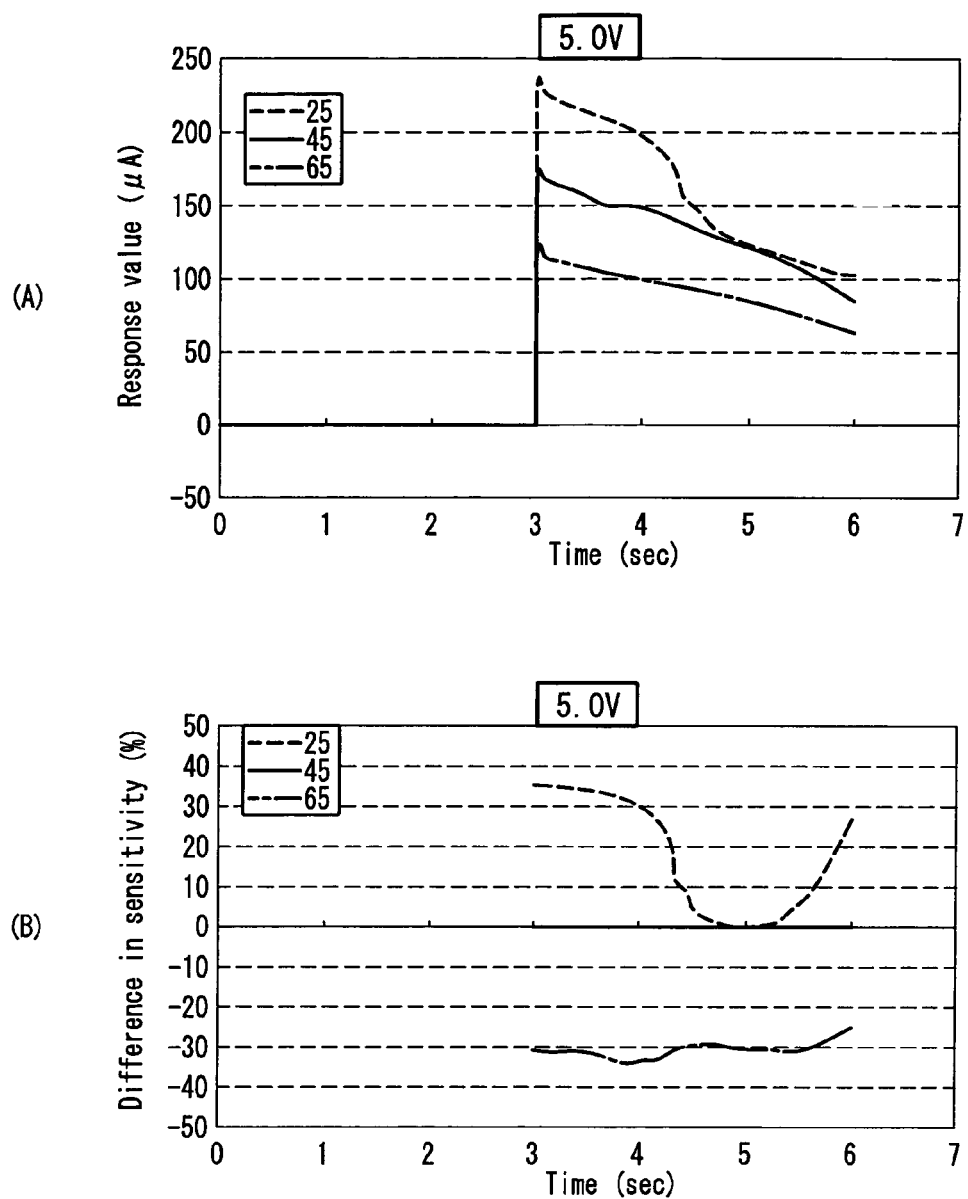
FIG. 28A is a graph showing changes in response current (A) over time during voltage application (5.0 V) in still another example of a sensor according to the present invention.
FIG. 28B is a graph showing changes in difference in sensitivity (%) over time during the voltage application in the example.
Figure 29:
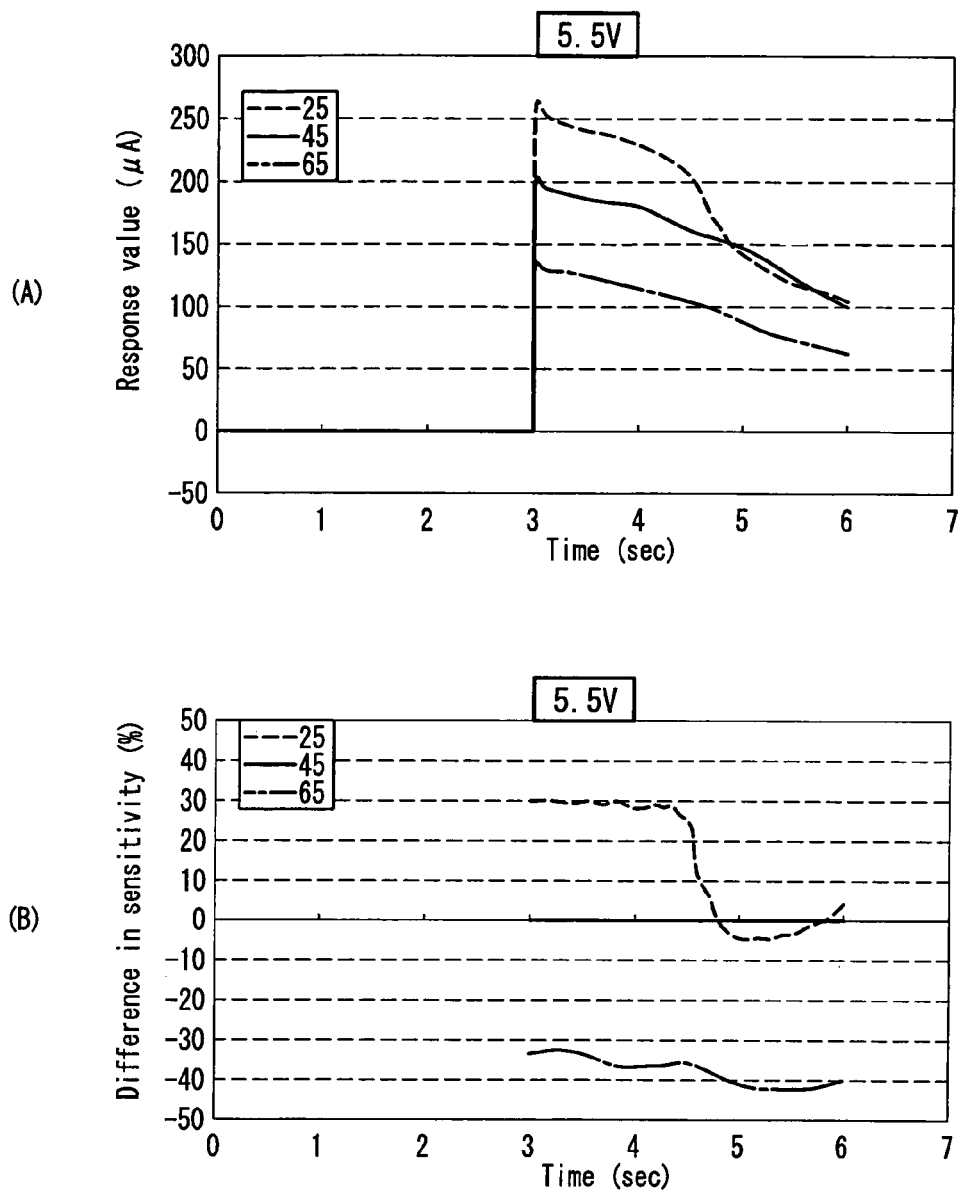
FIG. 29A is a graph showing changes in response current (A) over time during voltage application (5.5 V) in still another example of a sensor according to the present invention.
FIG. 29B is a graph showing changes in difference in sensitivity (%) over time during the voltage application in the example.
Figure 30:
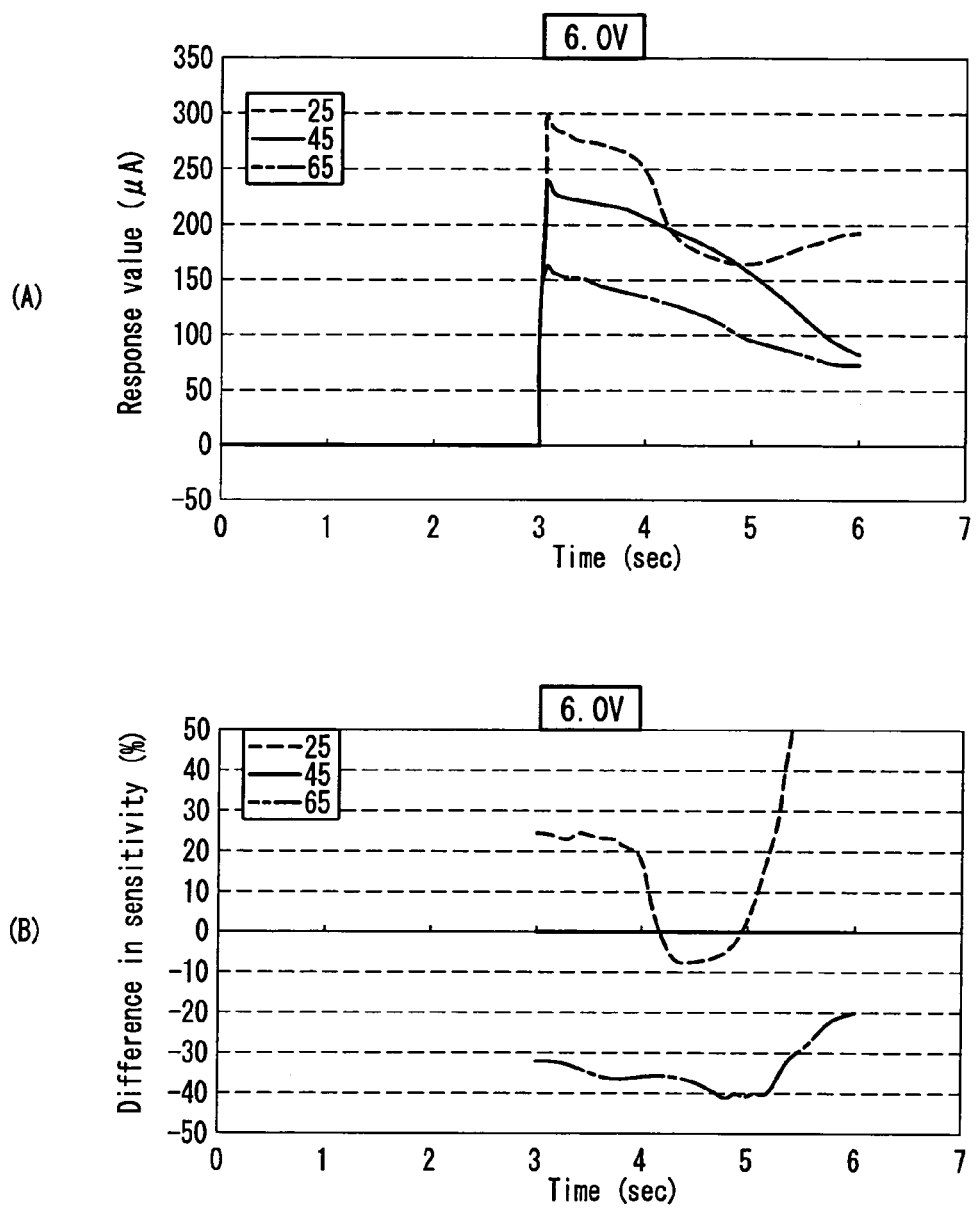
FIG. 30A is a graph showing changes in response current (A) over time during voltage application (6.0 V) in still another example of a sensor according to the present invention.
FIG. 30B is a graph showing changes in difference in sensitivity (%) over time during the voltage application in the example.
Figure 31:
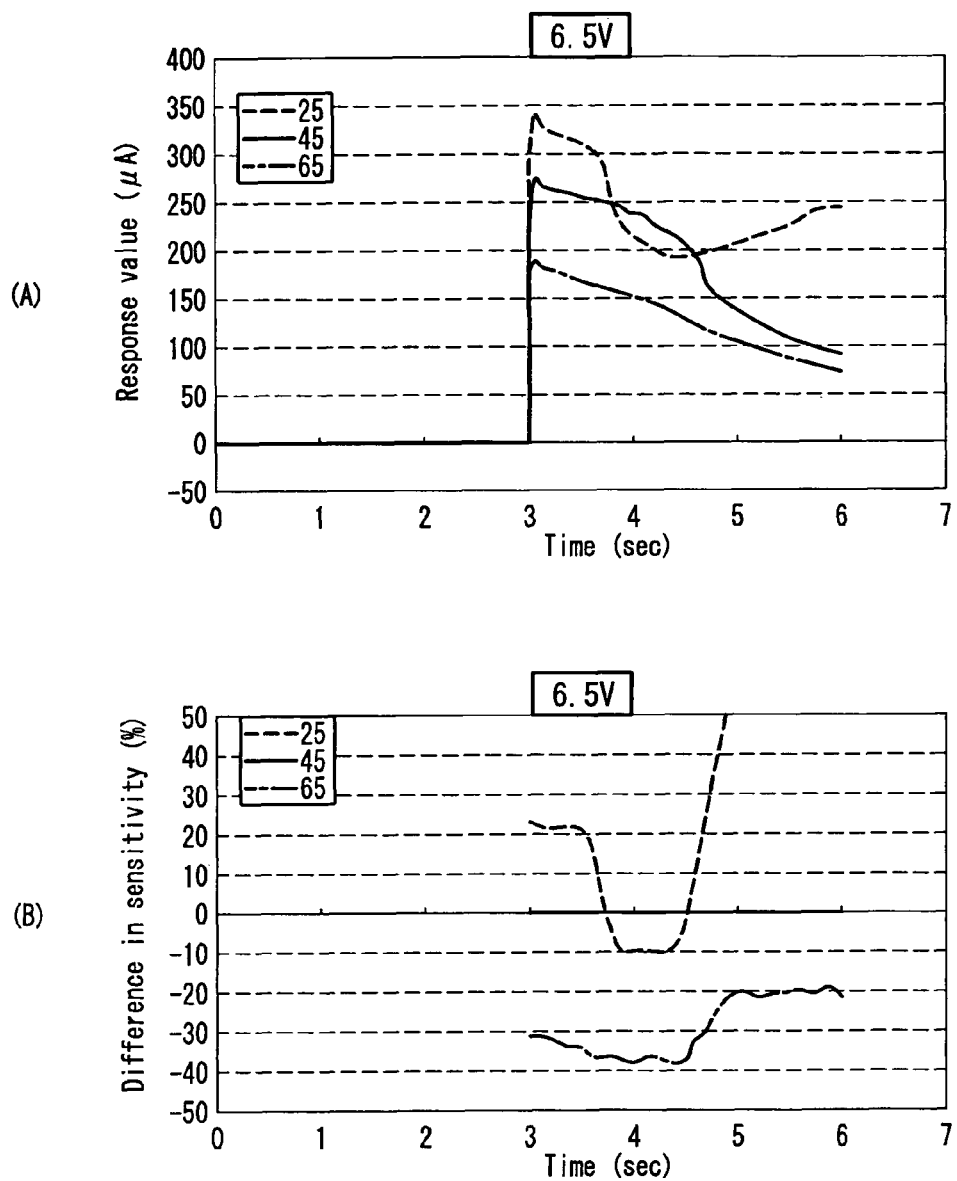
FIG. 31A is a graph showing changes in response current (A) over time during voltage application (6.5 V) in still another example of a sensor according to the present invention.
FIG. 31B is a graph showing changes in difference in sensitivity (%) over time during the voltage application in the example.

As shown in FIG. 19, even when the applied voltage was 0.5 V, it was possible to detect the response current reflecting the Hct value. However, as shown in FIGS. 20 to 31, the response current could be measured still more definitely when the applied voltage was in the range from 1 to 6.5 V. Furthermore, as shown in FIGS. 20 to 24, the most preferable results were obtained when the applied voltage was in the range from 1 to 3 V. When the applied voltage was 5 V or more, the distortion of the waveform occurred with the passage of time. However, within a short time immediately after the start of the voltage application, the response current reflecting the Hct value could be detected definitely. Although the present example is directed to the case where the current based on a Hct value was measured with various applied voltages under fixed conditions, the present invention is not limited thereto. It should be noted that even when the applied voltage is outside the range shown in the present example, it is still possible to detect the response current reflecting the Hct value definitely by setting other conditions such as the distance between the electrodes and the amount and the type of the redox substance as appropriate.

Example 4

Figure 32:
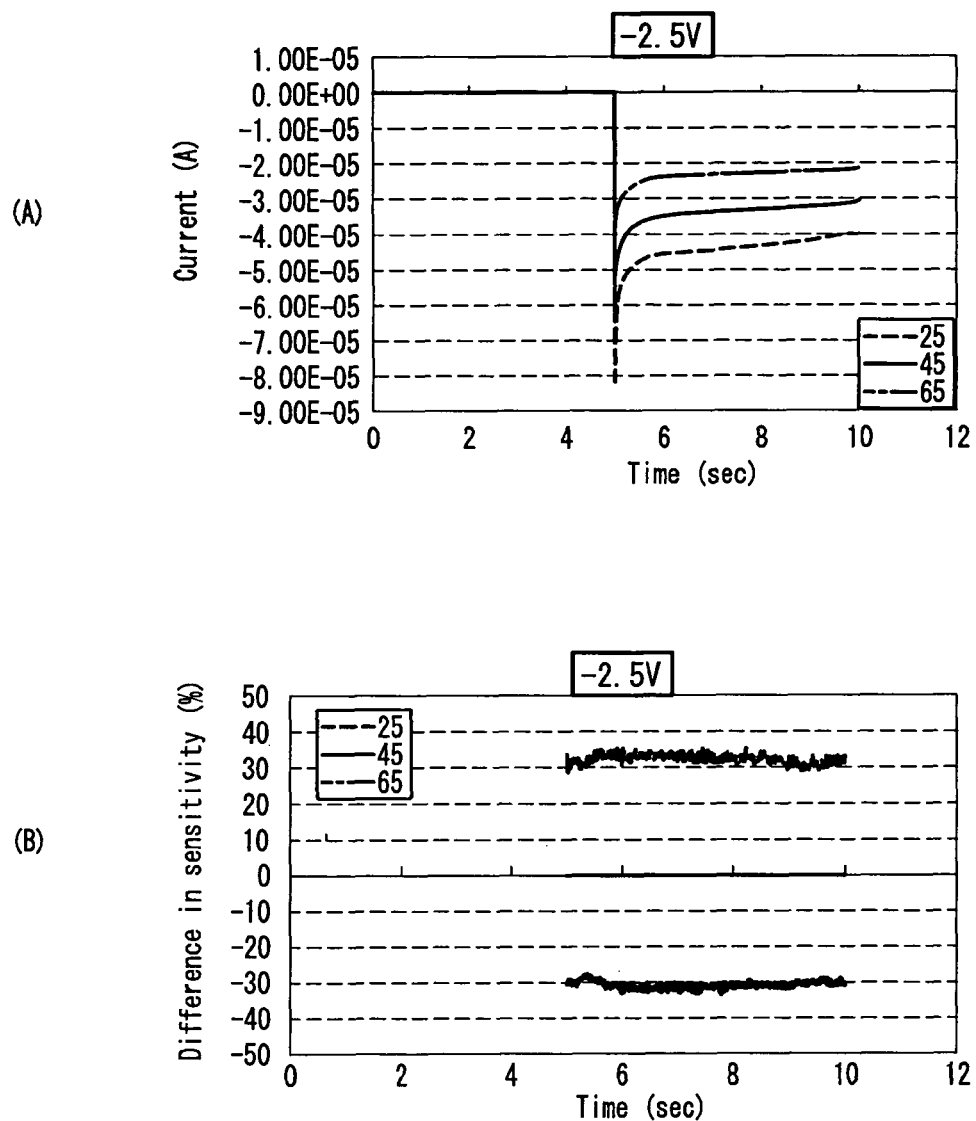
FIG. 32A is a graph showing changes in response current (A) over time during voltage application in still another example of a sensor according to the present invention.

A sensor having a configuration shown in FIGS. 1, 2, and 3 was produced. In this sensor, a working electrode 11 was coated with CMC. On the other hand, a reagent solution prepared by dissolving potassium ferrocyanide (amount: 60 mM) and taurine (80 mM) in a CMC aqueous solution (0.1 wt %) was dropped on a counter electrode 12 and then dried. The shortest distance between the electrodes was set to be at least 1.0 mm. Three types of blood samples whose Hct values were adjusted to be 25, 45, and 65, respectively, were provided. With regard to each of these three blood samples, a current flowing between the electrodes of the sensor when a voltage of −2.5 V was applied to the working electrode for 3 seconds was measured using the sensor. The results are shown in the graphs of FIG. 32A and FIG. 32B. FIG. 32A is a graph showing changes in response current (A) over time during the application of the voltage (V), and FIG. 32B is a graph showing changes in difference in sensitivity (%) over time during the application of the voltage (V). As shown in FIG. 32A and FIG. 32B, according to this sensor, the difference in sensitivity did not depend on the voltage application time, and the response current reflecting the Hct value could be detected definitely. Moreover, even in the case where a polymeric material such as CMC was not present on the electrodes, it was still possible to detect the current.

INDUSTRIAL APPLICABILITY

As specifically described above, according to a method of measuring a Hct value, a sensor used in the method, and a measuring device of the present invention, a Hct value can be measured electrochemically and easily with high accuracy and high reliability. Therefore, the measurement method, the sensor, and the measuring device of the present invention are useful for the measurement of the Hct value of blood and thus are suitable for the correction based on the Hct value in electrochemical measurement of a blood component such as glucose using a sensor.

The invention claimed is:

1. A method of electrochemically measuring a hematocrit (Hct) value of blood, comprising:
    supplying blood to an electrode system having a working electrode and a counter electrode, a redox substance being provided on the counter electrode but not on the working electrode;
    applying a voltage to the electrode system in this state to cause an oxidation current that does not depend on the redox substance or a reduction current that does not depend on the redox substance to flow between the electrodes;
    detecting the oxidation current or the reduction current; and
    determining a Hct value of the blood based on a value of the detected current.

2. The method according to claim 1, wherein the redox substance comprises a redox substance that is in at least one of an oxidized state and a reduced state.

3. The method according to claim 1, wherein the redox substance is a ferricyanide.

4. The method according to claim 1, wherein the redox substance is potassium ferricyanide.

5. The method according to claim 1, wherein the redox substance is a ferrocyanide.

6. The method according to claim 1, wherein the redox substance is potassium ferrocyanide.

7. The method according to claim 1, wherein the working electrode on which the redox substance is not provided is coated with a polymeric material.

8. The method according to claim 1, wherein the working electrode on which the redox substance is not provided is coated with carboxymethylcellulose.

9. The method according to claim 1, wherein the applied voltage is equal to or higher than a voltage causing electrolysis of water.

10. The method according to claim 1, wherein the applied voltage is 1 to 10 V.

11. The method according to claim 1, wherein the applied voltage is 1 to 6.5 V.

12. The method according to claim 1, wherein
    the redox substance is a ferrocyanide, and
    a voltage that is negative with respect to a voltage applied to the counter electrode is applied to the working electrode.

* * * * *